United States Patent
Kudou et al.

(10) Patent No.: US 9,676,703 B2
(45) Date of Patent: Jun. 13, 2017

(54) PRODUCTION METHOD FOR 3,3-DIMETHYL-3,4-DIHYDRO-1H-QUINOXALIN-2-ONE DERIVATIVE AND INTERMEDIATE FOR SAID PRODUCTION METHOD

(71) Applicant: SANTEN PHARMACEUTICAL CO., LTD., Osaka-shi, Osaka (JP)

(72) Inventors: Kazuhiro Kudou, Ikoma (JP); Masato Nagatsuka, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/910,971

(22) PCT Filed: Aug. 8, 2014

(86) PCT No.: PCT/JP2014/071053
§ 371 (c)(1),
(2) Date: Feb. 8, 2016

(87) PCT Pub. No.: WO2015/020204
PCT Pub. Date: Feb. 12, 2015

(65) Prior Publication Data
US 2016/0200690 A1 Jul. 14, 2016

(30) Foreign Application Priority Data
Aug. 9, 2013 (JP) .................................. 2013-166643

(51) Int. Cl.
C07D 241/44 (2006.01)
C07C 227/18 (2006.01)

(52) U.S. Cl.
CPC .......... *C07C 227/18* (2013.01); *C07D 241/44* (2013.01); *Y02P 20/55* (2015.11)

(58) Field of Classification Search
CPC .................................................. C07D 241/44
(Continued)

(56) References Cited

U.S. PATENT DOCUMENTS

| 6,369,057 B1 | 4/2002 | Billhardt et al. |
| 7,235,662 B2 | 6/2007 | Hadida-Ruah et al. |

(Continued)

FOREIGN PATENT DOCUMENTS

| JP | 5-148243 A | 6/1993 |
| JP | 2008-542281 A | 11/2008 |

(Continued)

OTHER PUBLICATIONS

International Search Report (PCT/ISA/210) mailed on Oct. 21, 2014, by the Japanese Patent Office as the International Searching Authority for International Application No. PCT/JP2014/071053.
(Continued)

Primary Examiner — Douglas M Willis
(74) Attorney, Agent, or Firm — Buchanan, Ingersoll & Rooney PC

(57) ABSTRACT

An object is to provide a novel production method suitable for industrial production of a 3,3-dimethyl-3,4-dihydro-1H-quinoxalin-2-one derivative and a synthetic intermediate for the method. Provided is a method for producing a compound represented by formula (1):

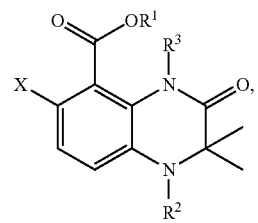

wherein $R^1$ represents a hydrogen atom, an optionally substituted alkyl group, an optionally substituted cycloalkyl group, or an optionally substituted aryl group, $R^2$ represents a hydrogen atom, an optionally substituted alkyl group, a hydroxy group, or nitrogen atom-protecting group, $R^3$ represents a hydrogen atom, an optionally substituted alkyl group, a hydroxy group, or a nitrogen atom-protecting group, and X represents a hydroxy group or a leaving group, or a salt thereof, the method comprising the steps of:
reacting a compound represented by formula (2):

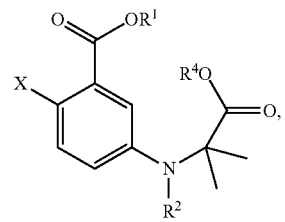

wherein $R^1$, $R^2$, and X are the same as defined in formula (1), $R^4$ represents an optionally substituted alkyl group, an optionally substituted cycloalkyl group, or an optionally substituted aryl group,
or a salt thereof with a nitrating agent to obtain a compound represented by formula (3):

(Continued)

wherein $R^1$, $R^2$, $R^4$, and X are the same as defined in formulae (1) and (2),
or a salt thereof, and
reducing the compound represented by formula (3) or the salt therof to obtain the compound represented by formula (1) or the salt thereof.

7 Claims, 3 Drawing Sheets

(58) Field of Classification Search
USPC .......................................................... 544/355
See application file for complete search history.

(56) References Cited

U.S. PATENT DOCUMENTS

| | | |
|---|---|---|
| 7,256,294 B2 | 8/2007 | Dalziel et al. |
| 7,405,299 B2 | 7/2008 | Beight et al. |
| 7,622,587 B2 | 11/2009 | Dalziel et al. |
| 7,723,326 B2 | 5/2010 | Lagu et al. |
| 7,759,363 B2 | 7/2010 | McKinnell et al. |
| 7,897,775 B2 | 3/2011 | Dalziel et al. |
| 8,143,279 B2 | 3/2012 | McKinnell et al. |
| 8,232,288 B2 | 7/2012 | Schunk et al. |
| 8,288,550 B2 | 10/2012 | Dalziel et al. |
| 8,377,964 B2 | 2/2013 | McKinnell et al. |
| 2004/0266758 A1 | 12/2004 | Hadida-Ruah et al. |
| 2006/0058295 A1 | 3/2006 | Beight et al. |
| 2006/0270652 A1 | 11/2006 | McKinnell et al. |
| 2006/0270854 A1 | 11/2006 | Dalziel et al. |
| 2007/0078129 A1 | 4/2007 | Lagu et al. |
| 2007/0244157 A1 | 10/2007 | Dalziel et al. |
| 2009/0111807 A1 | 4/2009 | Matsuda et al. |
| 2009/0209582 A1 | 8/2009 | McKinnell et al. |
| 2010/0029946 A1 | 2/2010 | Dalziel et al. |
| 2010/0249186 A1 | 9/2010 | McKinnell et al. |
| 2011/0009382 A1 | 1/2011 | Schunk et al. |
| 2011/0201644 A1 | 8/2011 | Dalziel et al. |
| 2013/0273568 A1 | 10/2013 | McKinnell et al. |
| 2013/0303537 A1 | 11/2013 | Matsuda et al. |
| 2015/0183761 A1 | 7/2015 | McKinnell et al. |

FOREIGN PATENT DOCUMENTS

| | | |
|---|---|---|
| JP | 2009-513570 A | 4/2009 |
| JP | 2012-529448 A | 11/2012 |
| WO | WO 2004/050659 A1 | 6/2004 |
| WO | WO 2004-110385 A2 | 12/2004 |
| WO | WO 2007/105766 A1 | 9/2007 |

OTHER PUBLICATIONS

Written Opinion (PCT/ISA/237) mailed on Oct. 21, 2014, by the Japanese Patent Office as the International Searching Authority for International Application No. PCT/JP2014/071053.
STN International, 5-Quinoxalinecarboxylic acid, 1-ethyl-1,2,3,4-tetrahydro-2,2-dimethyl-3-oxo-, file REGISTRY [online], Feb. 24, 2014, [retrieved on Oct. 6, 2014 (Oct. 6, 2014)], CAS Registry No. 1553610-11-9 (3 pages).
STN International, 5-Quinoxalinecarboxylic acid, 1,2,3,4-tetrahydro-2,2-dimethyl-3-oxo-, file REGISTRY [online], Feb. 20, 2014, [retrieved on Oct. 6, 2014 (Oct. 6, 2014)], CAS Registry No. 1550624-47-9 (2 pages).
STN International, 5-Quinoxalinecarboxylic acid, 1,2,3,4-tetrahydro-1,2,2-trimethyl-3-oxo-, file REGISTRY [online], Feb. 17, 2014, [retrieved on Oct. 6, 2014 (Oct. 6, 2014)], CAS Registry No. 1547188-08-8 (2 pages).

PRODUCTION METHOD FOR 3,3-DIMETHYL-3,4-DIHYDRO-1H-QUINOXALIN-2-ONE DERIVATIVE AND INTERMEDIATE FOR SAID PRODUCTION METHOD

BACKGROUND OF THE INVENTION (1) Field of the Invention

The present invention relates to a method for producing a 3,3-dimethyl-3,4-dihydro-1H-quinoxalin-2-one derivative and also to intermediates for the production method.

(2) Description of the Related Art

As a 3,3-dimethyl-3,4-dihydro-1H-quinoxalin-2-one derivative, for example, Patent Literature 1 discloses 7-bromo-8-methoxycarbonyl-3,3-dimethyl-,4-dihydro-1H-quinoxalin-2-one (compound (H) in FIG. 1), which is known as a synthetic intermediate of a 1,2,3,4-tetrahydroquinoxaline derivative having a binding activity to the glucocorticoid receptor.

In addition, Patent Literature 1 discloses a method for synthesizing 7-bromo-8-methoxycarbonyl-3,3-dimethyl-3, 4-dihydro-1H-quino xalin-2-one (compound (H)) in Reference Example 1 (FIG. 1).

CITATION LIST

Patent Literature

Patent Literature 1: International Publication No. WO 2007/105766

BRIEF SUMMARY OF THE INVENTION

However, the above-described method has the following problems (1) to (3), and has to be further improved for employment of this method as an industrial production method.

(1) In the alkylation reaction of Step 5, it is neccesary to use an excessive amount of compound (F) as the reaction solvent. In addition, this reaction takes a long period with the reaction time being four days, results in a low yield (31%), and also requires purification by column chromatography.

(2) In also Steps 3 and 6 in FIG. 1, purification by column chromatography is necessary.

(3) This process is long with the number of steps being six in total.

Accordingly, an object of the present invention is to provide a novel production method suitable for industrial production of a 3,3-dimethyl-3, 4-dihydro-1H-quinoxalin-2-one derivative and a synthetic intermediate for the method.

Solution to Problems

The present inventor has conducted intensive study, and consequently has found that the use of a novel intermediate compound (2) for synthesizing a compound represented by formula (1) or a salt thereof (hereinafter, also referred to as "compound (1)", and the same all apply to compounds represented by formulae denoted by other numbers and salts thereof) makes it possible to obtain compound (3) and compound (1) highly efficiently without purification by column chromatography (see FIG. 2). It has been also found that the reaction of compound (4) with compound (5) or (5) ' makes it possible to efficiently obtain compound (2) in a high yield without using an excessive amount of compound (5) or (5)' in contrast to the above-described prior art (Step 5 in FIG. 1), without using compound (5) or (5)' as the reaction solvent, and without requiring a purification step by column chromatography (see FIG. 2). Moreover, it has been found that the target compound (1) can be obtained from the raw material compound (4) through three to four steps in total.

In addition, it has been found that the target compound (1) can be obtained through two steps in total by reacting compound (9) with compound (5)" to obtain compound (8), which is a precursor of compound (1), and then introducing a leaving group to the 7-position of the precursor compound (8) (see FIG. 3).

Moreover, novel intermediates for those production methods have been found.

Specifically, the present invention is as follows:

[1] A method for producing a compound represented by formula (1):

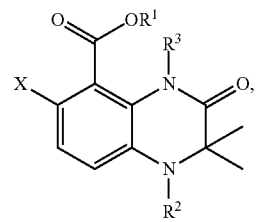

wherein $R^1$ represents a hydrogen atom, an optionally substituted alkyl group, an optionally substituted cycloalkyl group, or an optionally substituted aryl group, $R^2$ represents a hydrogen atom, an optionally substituted alkyl group, a hydroxy group, or a nitrogen atom-protecting group, $R^3$ represents a hydrogen atom, an optionally substituted alkyl group, a hydroxy group, or a nitrogen atom-protecting group, and X represents a hydroxy group or a leaving group, or a salt thereof, the method comprising the steps of:

reacting a compound represented by formula (2):

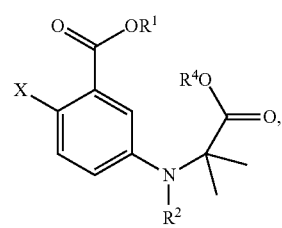

wherein $R^1$, $R^2$, and X are the same as defined in formula (1), and $R^4$ represents an optionally substituted alkyl group, an optionally substituted cycloalkyl group, or an optionally substituted aryl group, or a salt thereof with a nitrating agent to obtain a compound represented by formula (3):

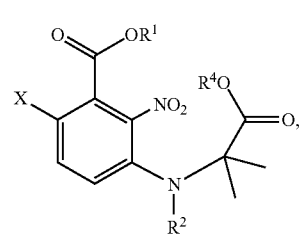

wherein $R^1$, $R^2$, $R^4$, and X are the same as defined in formulae (1) and (2), or a salt thereof; and reducing the compound represented by formula (3) or the salt thereof to obtain the compound represented by formula (1) or the salt thereof.

[2] The production method according to [1], further comprising the step of reacting a compound represented by formula (6):

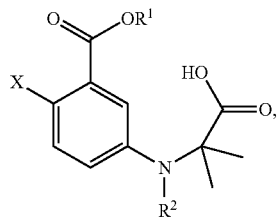

wherein $R^1$, $R^2$, and X are the same as defined in formula (1), or a salt thereof with

$R^4OH$ (7), wherein $R^4$ is the same as defined in formula (2), in the presence of an acid to obtain the compound represented by formula (2) or the salt thereof.

[3] The production method according to [2], wherein $R^1$ in formula (6) is a hydrogen atom.

[4] The production method according to [2] or [3], further comprising the step of reacting a compound represented by formula (4):

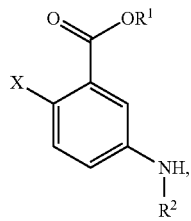

wherein $R^1$, $R^2$, and X are the same as defined in formula (1), or a salt thereof with a compound represented by formula (5):

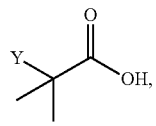

wherein Y represents a hydroxy group or a leaving group, or a salt thereof to obtain the compound represented by formula (6) or the salt thereof.

[5] The production method according to [1], further comprising the step of reacting a compound represented by formula (4):

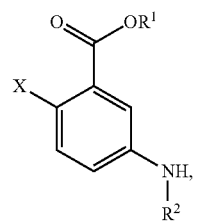

wherein $R^1$, $R^2$, and X are the same as defined in formula (1), or a salt thereof with a compound represented by formula (5)':

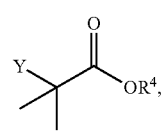

wherein $R^4$ is the same as defined in formula (2), and Y represents a hydroxy group or a leaving group, or a salt thereof to obtain the compound represented by formula (2) or the salt thereof.

[6] A method for producing a compound represented by formula (2):

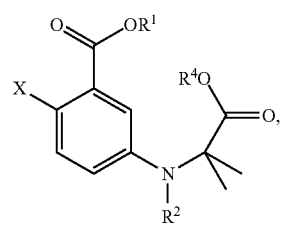

wherein $R^1$ represents a hydrogen atom, an optionally substituted alkyl group, an optionally substituted cycloalkyl group, or an optionally substituted aryl group, $R^2$ represents a hydrogen atom, an optionally substituted alkyl group, a hydroxy group, or a nitrogen atom-protecting group, $R^4$ represents an optionally substituted alkyl group, an optionally substituted cycloalkyl group, or an optionally substituted aryl group, and X represents a hydroxy group or a leaving group, or a salt thereof, the method comprising the step of reacting a compound represented by formula (6):

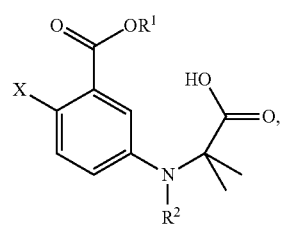

wherein $R^1$, $R^2$, and X are the same as defined in formula (2), or a salt thereof with

$R^4OH$ (7), wherein $R^4$ is the same as defined in formula (2), in the presence of an acid to obtain the compound represented by formula (2) or the salt thereof.

[7] The production method according to [6], wherein R$^1$ in formula (6) is a hydrogen atom.

[8] The production method according to [6] or [7], further comprising the step of reacting a compound represented by formula (4):

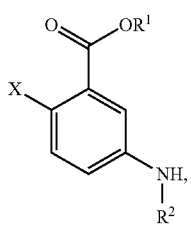

wherein R$^1$, R$^2$, and X are the same as defined in formula (2), or a salt thereof with a compound represented by formula (5):

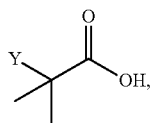

wherein Y represents a hydroxy group or a leaving group, or a salt thereof to obtain the compound represented by formula (6) or the salt thereof.

[9] A method for producing a compound represented by formula (2):

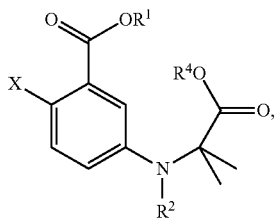

wherein R$^1$ represents a hydrogen atom, an optionally substituted alkyl group, an optionally substituted cycloalkyl group, or an optionally substituted aryl group, R$^2$ represents a hydrogen atom, an optionally substituted alkyl group, a hydroxy group, or a nitrogen atom-protecting group, R$^4$ represents an optionally substituted alkyl group, an optionally substituted cycloalkyl group, or an optionally substituted aryl group, and X represents a hydroxy group or a leaving group, or a salt thereof, the method comprising the step of reacting a compound represented by formula (4):

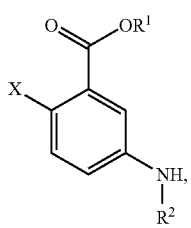

wherein R$^1$, R$^2$, and X are the same as defined in formula (2), or a salt thereof with a compound represented by formula (5)':

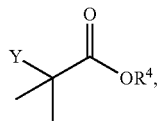

wherein R$^4$ is the same as defined in formula (2), and Y represents a hydroxy group or a leaving group, or a salt thereof to obtain the compound represented by formula (2) or the salt thereof.

[10] A compound represented by formula (2) or a salt thereof:

(2)

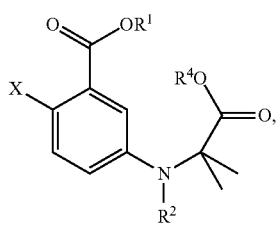

wherein R$^1$ represents a hydrogen atom, an optionally substituted alkyl group, an optionally substituted cycloalkyl group, or an optionally substituted aryl group, R$^2$ represents a hydrogen atom, an optionally substituted alkyl group, a hydroxy group, or a nitrogen atom-protecting group, R$^4$ represents an optionally substituted alkyl group, an optionally substituted cycloalkyl group, or an optionally substituted aryl group, and X represents a hydroxy group or a leaving group.

[11] The compound or the salt thereof according to [10], wherein the compound represented by formula (2) or the salt thereof is methyl 2-bromo-5-(1-methoxycarbonyl-1-methylethyl)aminobenzoate.

[12] A compound represented by formula (6) or a salt thereof:

(6)

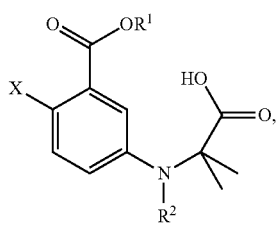

wherein R$^1$ represents a hydrogen atom, an optionally substituted alkyl group, an optionally substituted cycloalkyl group, or an optionally substituted aryl group, R$^2$ represents a hydrogen atom, an optionally substituted alkyl group, a hydroxy group, or a nitrogen atom-protecting group, and X represents a hydroxy group or a leaving group.

[13] The compound [12] or the salt thereof according to, wherein the compound represented by formula (6) or the salt thereof is selected from the group consisting of 2-bromo-5-(1-carboxy-1-methylethyl)aminobenzoic acid and methyl 2-bromo-5-(1-carboxy-1-methylethyl)aminobenzoate.

[14] A method for producing a compound represented by formula (1):

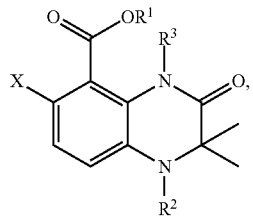

wherein R¹ represents a hydrogen atom, an optionally substituted alkyl group, an optionally substituted cycloalkyl group, or an optionally substituted aryl group, R² represents a hydrogen atom, an optionally substituted alkyl group, a hydroxy group, or a nitrogen atom-protecting group, R³ represents a hydrogen atom, an optionally substituted alkyl group, a hydroxy group, or a nitrogen atom-protecting group, and X represents a hydroxy group or a leaving group, or a salt thereof, the method comprising the step of introducing X, which is the same as defined in formula (1), to a compound represented by formula (8):

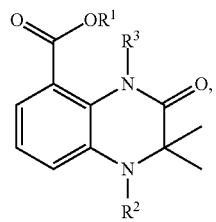

wherein R¹, R² and R³ are the same as defined in formula (1), or a salt thereof.

[15] The production method according to [14], wherein the step of introducing X is conducted by reacting the compound represented by formula (8) or the salt thereof with a halogenating agent selected from the group consisting of chlorine, bromine, 1,3-dibromo-5,5-dimethylhydantoin, N-chlorosuccinimide, N-bromosuccinimide, tetrabutylammonium tribromide, dimethylaminopyridine tribromide, and 2,4,4,6-tetrabromo-2,5-cyclohexadienone.

[16] The production method according to [14] or [15], further comprising the step of reacting a compound represented by formula (9):

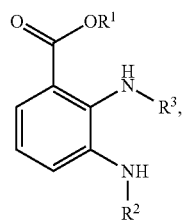

wherein R¹, R², and R³ are the same as defined in formula (8), or a salt thereof with a compound represented by formula (5)":

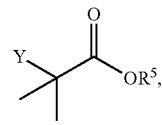

wherein R⁵ represents a hydrogen atom, an optionally substituted alkyl group, an optionally substituted cycloalkyl group, or an optionally substituted aryl group, and Y represents a hydroxy group or a leaving group, or a salt thereof to obtain the compound represented by formula (8) or the salt thereof.

[17] A method for producing a compound represented by formula (8):

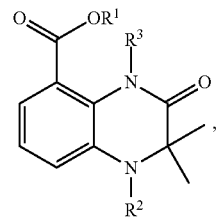

wherein R¹ represents a hydrogen atom, an optionally substituted alkyl group, an optionally substituted cycloalkyl group, or an optionally substituted aryl group, R² represents a hydrogen atom, an optionally substituted alkyl group, a hydroxy group, or a nitrogen atom-protecting group, and R³ represents a hydrogen atom, an optionally substituted alkyl group, a hydroxy group, or a nitrogen atom-protecting group, or a salt thereof, the method comprising the step of reacting a compound represented by formula (9):

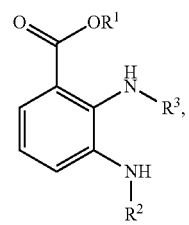

wherein R¹, R², and R³ are the same as defined in formula (8), or a salt thereof with a compound represented by formula (5)":

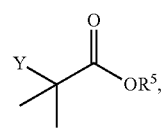

wherein R⁵ represents a hydrogen atom, an optionally substituted alkyl group, an optionally substituted cycloalkyl group, or an optionally substituted aryl group, and Y represents a hydroxy group or a leaving group, or a salt thereof to obtain the compound represented by formula (8) or the salt thereof.

[18] A compound represented by formula (8) or a salt thereof:

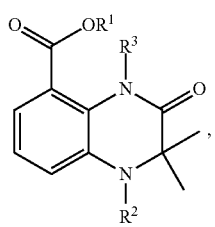

(8)

wherein R¹ represents a hydrogen atom, an optionally substituted alkyl group, an optionally substituted cycloalkyl group, or an optionally substituted aryl group, R² represents a hydrogen atom, an optionally substituted alkyl group, a hydroxy group, or a nitrogen atom-protecting group, and R³ represents a hydrogen atom, an optionally substituted alkyl group, a hydroxy group, or a nitrogen atom-protecting group.

[19] The compound or the salt thereof according to [18], wherein
the compound represented by formula (8) or the salt thereof is 8-methoxycarbonyl-3,3-dimethyl-3,4-dihydro-1H-quinoxalin-2-one.

The use of the novel intermediate compound (2) in the production method of the present invention makes it possible to obtain compound (3) and compound (1) highly efficiently without purification by column chromatography. In addition, the reaction of compound (4) with compound (5) or (5)' makes it possible to efficiently obtain compound (2) in a high yield without using an excessive amount of compound (5) or (5)' in contrast to the above-described prior art (Step 5 in FIG. 1), without using compound (5) or (5)' as the reaction solvent, and without requiring a purification step by column chromatography (see FIG. 2). Moreover, the target compound (1) can be obtained from the raw material compound (4) through three to four steps in total.

In addition, the target compound (1) can be obtained through two steps in total by reacting compound (9) with compound (5)" to obtain compound (8), which is a precursor of compound (1), and then introducing a leaving group to the 7-position of the precursor compound (8) (see FIG. 3).

Moreover, novel intermediates for these production methods can be provided.

DETAILED DESCRIPTION OF THE INVENTION

Figure 1:
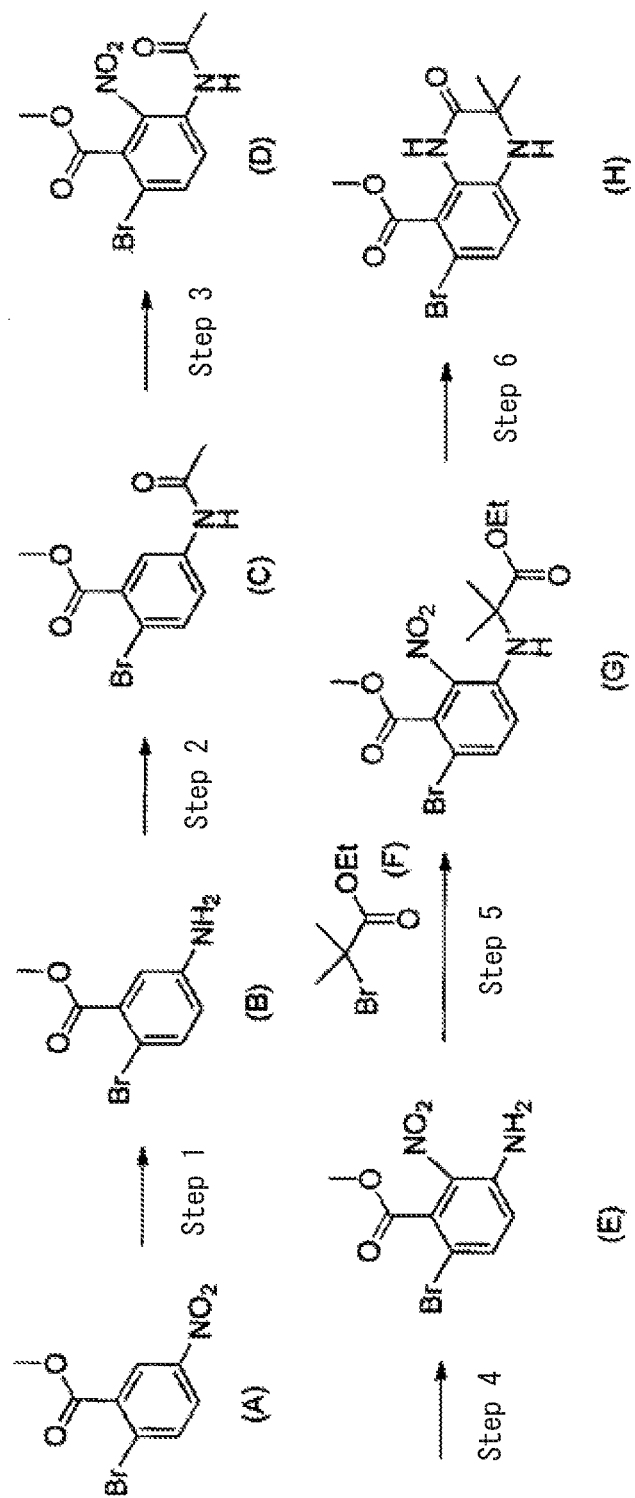
FIG. 1 shows steps of producing 7-bromo-8-methoxycarbonyl-3,3-dilmethyl-3 4-dihydro-1H-quinoxalin-2-one according to a conventional technique.

Hereinafter, definitions of atoms, groups, rings, and the like used herein are described in detail. In addition, when the definition of a wording described below is applied mutatis mutandis to the definition of another wording, the definition can also be applied mutatis mutandis to the preferred range and the particularly preferred range.

A "halogen atom" means a fluorine atom, a chlorine atom, a bromine atom, or an iodine atom.

An "alkyl group" means a linear or branched saturated hydrocarbon group, and, for example may be a "$C_{1-12}$ alkyl group", a "$C_{1-8}$ alkyl group," or a "$C_{1-6}$ alkyl group." The "$C_{1-12}$ alkyl group," the "$C_{1-8}$ alkyl group," and the "$C_{1-6}$ alkyl group" mean alkyl groups whose numbers of carbon atoms are 1 to 12, 1 to 8, and 1 to 6, respectively. Specific examples thereof include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, a n-heptyl group, a n-octyl group, and the like.

A "cycloalkyl group" means a monocyclic saturated hydrocarbon group, and, for example, may be a "$C_{3-8}$ cycloalkyl group" or a "$C_{3-6}$ cycloalkyl group." The "$C_{3-8}$ cycloalkyl group" and the "$C_{3-6}$ cycloalkyl group" mean cycloalkyl groups whose numbers of carbon atoms are 3 to 8, and preferably 3 to 6, respectively. Specific examples thereof include a cyclopropyl group, a cyclobutyl group, a cyclopentyl group, a cyclohexyl group, a cycloheptyl group, a cyclooctyl group, and the like.

An "aryl group" means a residue obtainable by removing one hydrogen atom from a monocyclic aromatic hydrocarbon or bicyclic or tricyclic condensed-polycyclic aromatic hydrocarbon having 6 to 14 carbon atoms. Specific examples thereof include a phenyl group, a naphthyl group, an anthryl group, a phenanthryl group, and the like.

A "nitrogen atom-protecting group" means a substituent which protects a nitrogen atom, and which allows a nitrogen-hydrogen bond to be formed under suitable deprotection conditions. Specific examples thereof include protective groups described in Philip J. Kocienski, Protecting Groups (1994), or P. G. M. Wuts and T. W. Greene, "Greene's Protective Groups in Organic Synthesis (Fourth Edition, 2006), and the like. Examples of the protecting groups include $C_{1-8}$ alkoxycarbonyl groups (for example, a methoxycarbonyl group, an ethoxycarbonyl group, a t-butoxycarbonyl group, and the like), a benzyloxycarbonyl group, a methoxymethyl group, a benzyl group, an o-methoxybenzyl group, a p-methoxybenzyl group, a formyl group, a trifluoroacetyl group, a 1,2-dioxoethyl group, a 1,2-dioxobutyl group, a 2-methoxy-1-oxoethyl group, a 2-phenyl-1-oxoethyl group, a 2-acetyloxy-1-oxoethyl group, a 2-amino-1-oxoethyl group, a phenoxycarbonyl group, a 2-acetyloxyphenyloxycarbonyl group, a 2-acetyloxybenzyloxycarbonyl group, a {[1-(acetyloxy)ethyl]oxy}carbonyl group, a ({1-[(2-methylpropanoyl)oxy]ethyl}oxy)carbonyl group, a ({1-[(2,2-dimethylpropanoyl)oxy]ethyl}oxy)carbonyl, a (methylsulfonyl)carbamoyl group, a (phenylsulfonyl)carbamoyl group, a (4-methylphenylsulfonyl)carbamoyl group, and the like.

A "leaving group" means a substituent which is eliminated by a reaction. Specific examples thereof include halogen atoms, alkylsulfonyloxy groups, arylsulfonyloxy groups, a cyano group, a nitro group, trichloroacetimidate, and the like.

An "alkylsulfonyl group" means a group in which the hydroxy group of a sulfonic acid group is replaced with an alkyl group. Specific examples thereof include a methylsulfonyl group, a chloromethylsulfonyl group, a trifluoromethylsulfonyl group, an ethylsulfonyl group, a n-propylsulfonyl group, a n-butylsulfonyl group, a n-pentylsulfonyl group, a n-hexylsulfonyl group, a n-heptylsulfonyl group, a n-octylsulfonyl group, an isopropylsulfonyl group, an isobutylsulfonyl group, a sec-butylsulfonyl group, a tert-butylsulfonyl group, an isopentylsulfonyl group, and the like.

An "arylsulfonyl group" means a group in which the hydroxy group of a sulfonic acid group is replaced with an aryl group. Specific examples thereof include a phenylsulfonyl group, a p-toluenesulfonyl group, a naphthylsulfonyl group, an anthrylsulfonyl group, a phenanthrylsulfonyl group, and the like.

An "alkylsulfonyloxy group" means a group in which the hydrogen atom of a hydroxy group is replaced with an alkylsulfonyl group. Specific examples thereof include a methylsulfonyloxy group, a chloromethylsulfonyloxy group, a trifluoromethylsulfonyloxy group, an ethylsulfonyloxy group, a n-propylsulfonyloxy group, a n-butylsulfonyloxy group, a n-pentylsulfonyloxy group, a n-hexysulfonyloxy group, a n-heptylsulfonyloxy group, a n-octylsulfonyloxy group, an isopropylsulfonyloxy group, an isobutylsulfonyloxy group, a sec-butylsulfonyloxy group, a tert-butylsulfonyloxy group, an isopentylsulfonyloxy group, and the like.

An "arylsulfonyloxy group" means a group in which the hydrogen atom of a hydroxy group is replaced with an arylsulfonyl group. Specific examples thereof include a phenylsulfonyloxy group, a p-toluenesulfonyloxy group, a naphthylsulfonyloxy group, an anthrylsulfonyloxy group, a phenanthrylsulfonyloxy group, and the like.

An "optionally substituted alkyl group," an "optionally substituted cycloalkyl group," and an "optionally substituted aryl group" respectively mean an "alkyl group," a "cycloalkyl group," and an "aryl group" each optionally having any one or multiple substituent groups.

The "multiple groups" may be the same or different from each other. The number of the groups is preferably 1, 2, or 3, and is particularly preferably 2. In addition, the concept of the "groups" also includes hydrogen atoms and halogen atoms.

Raw materials and reagents used in the present invention and other compounds described herein may form "salts" with acids or bases. Specific examples of the salts include salts with an inorganic acid such as hydrochloric acid, hydrobromic acid, bromic acid, hydroiodic acid, nitric acid, sulfuric acid, or phosphoric acid; salts with an organic acid such as carbonic acid, acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, 10-camphorsulfonic acid, sulfuric acid lauryl ester, methyl sulfate, naphthalenesulfonic acid, or sulfosalicylic acid; quaternary ammonium salts of methyl bromide, methyl iodide, or the like; salts with a halogen ion such as a bromine ion, a chlorine ion, or an iodine ion; salts with an alkali metal such as lithium, sodium, or potassium; salts with an alkaline earth metal such as calcium or magnesium; salts with a metal such as copper, iron, or zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-dimethylaniline, or N,N-bis(phenylmethyl)-1,2-ethanediamine; salts with pyridine; and the like.

The raw materials and reagents used in the present invention and other compounds described herein may be in the form of hydrates or solvates.

When geometric isomers or optical isomers are present for any of the raw materials and reagents used in the present invention and other compounds described herein, these isomers are also included within the scope of the present invention.

When any of the raw materials and reagents used in the present invention and other compounds described herein undergoes proton tautomerization, the tautomers are also included within the present invention.

The raw materials and reagents used in the present invention and other compounds described herein, the hydrates thereof, and the solvates thereof may each be in the form of a crystal. When the crystal exhibits polymorphism, and a polymorphic group (a polymorphic system) exists, the polymorphs and the polymorphic group (polymorphic system) are also included within the present invention. Here, the polymorphic group (polymorphic system) means the crystal form in each stage in a case where the crystal form changes according to the conditions in the production, crystallization, storage, and the like of the crystal and on the state (note that the state also include a state of being prepared into a pharmaceutical preparation) of the crystal, as well as the entire process.

Hereinafter, a method for producing compound (1) is described.

Figure 2:
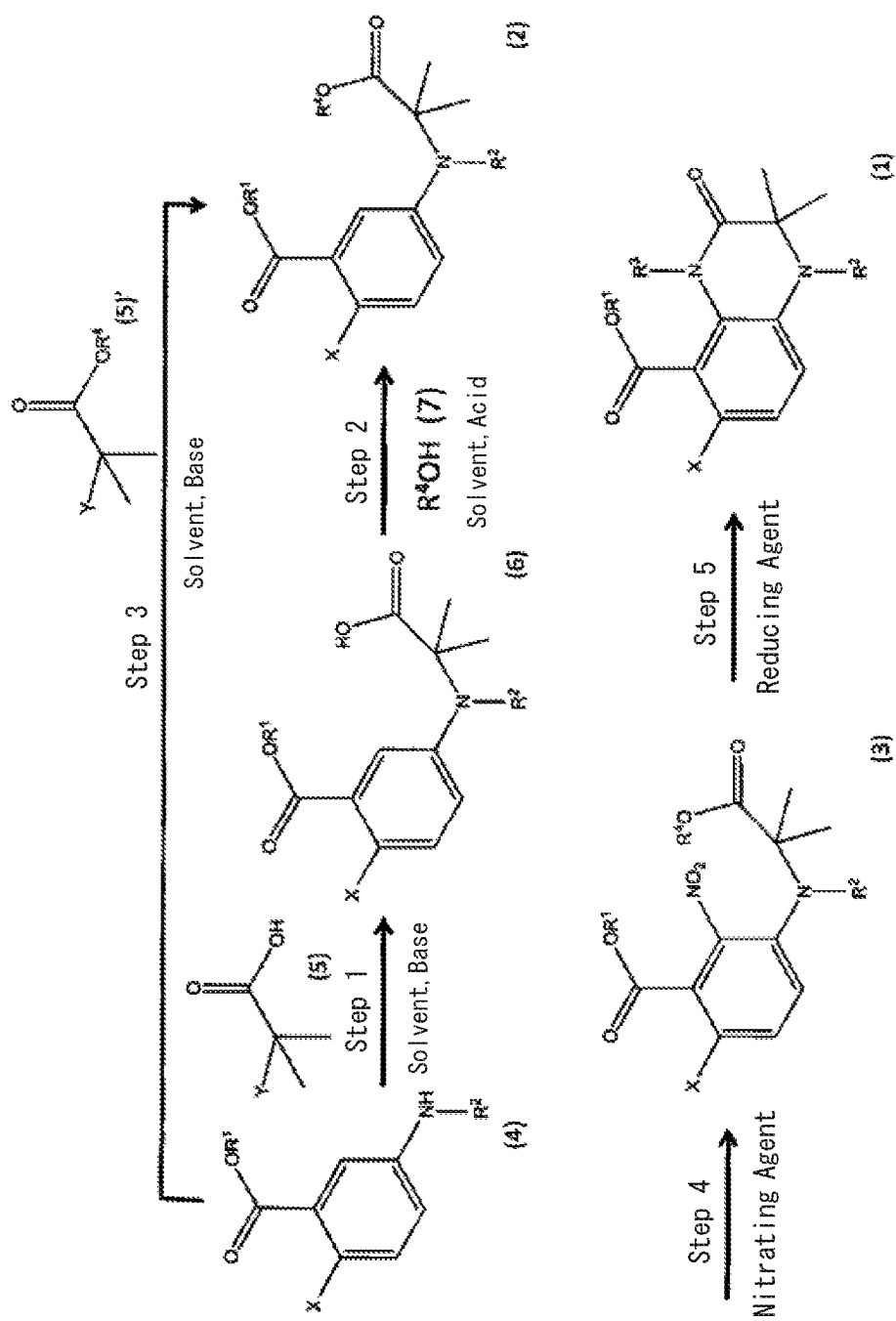
FIG. 2 shows production steps in Method 1 for producing compound (1).

[Production Method 1] (See FIG. 2)

Hereinafter, a description will be given of a method for producing compound (1) from a raw material compound (4) and a raw material compound (5) or (5)' optionally through a novel compound (6) and a novel compound (2). Specifically, a description will be given of each of Step 1 of producing compound (6) by using compound (4) and compound (5) as raw materials, Step 2 of producing compound (2) from compound (6) and compound (7), Step 3 of producing compound (2) from compound (4) and compound (5)', Step 4 of producing compound (3) from compound (2), and Step 5 of producing compound (1) from compound (3).

<Step 1>

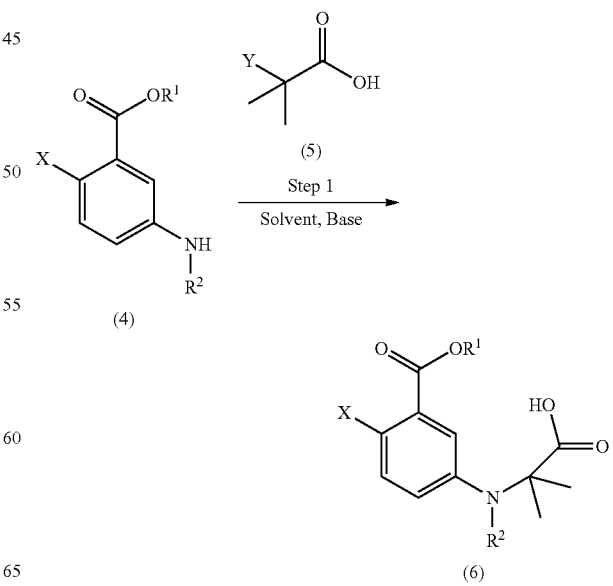

Step 1 is a step of producing compound (6) by reacting compound (4) with compound (5) in a solvent in the presence of a base. Note that, as compound (4), one that is commercially available or produced by a known method can be used.

In formulae (4) and (6), $R^1$ represents a hydrogen atom, an optionally substituted alkyl group, an optionally substituted cycloalkyl group, or an optionally substituted aryl group, and is preferably a hydrogen atom or an optionally substituted alkyl group, and more preferably a hydrogen atom. $R^2$ represents a hydrogen atom, an optionally substituted alkyl group, a hydroxy group, or a nitrogen atom-protecting group, and is preferably a hydrogen atom or a nitrogen atom-protecting group, and more preferably a hydrogen atom. X represents a hydroxy group or a leaving group, and is preferably a leaving group, more preferably a halogen atom, and further preferably a bromine atom. In formula (5), Y represents a hydroxy group or a leaving group, and is preferably a leaving group, more preferably a halogen atom, and further preferably a bromine atom.

Compound (5) is used in an amount of, for example, 1 mole equivalent or more but 3 mole equivalents or less, preferably 1 to 2 mole equivalents, and particularly preferably 1.2 to 1.5 mole equivalents relative to compound (4).

The solvent used in Step 1 is not particularly limited, as long as the solvent does not inhibit the reaction and can dissolve the starting substances to some degree. Preferred examples of the solvent include aromatic hydrocarbons, halogenated hydrocarbons, ethers, lower-alkylcarboxylic esters, amides, sulfoxides, lower alcohols, water, and mixture solvents thereof. The aromatic hydrocarbons include benzene, toluene, xylene, and the like. The halogenated hydrocarbons include dichloromethane, chloroform, carbon tetrachloride, dichloroethane, chlorobenzene, dichlorobenzene, and the like. The ethers include diethyl ether, diisopropyl ether, tetrahydrofuran, cyclopentyl methyl ether, methyl tert-butyl ether, dioxane, dimethoxyethane, diethylene glycol dimethyl ether, and the like. The lower-alkylcarboxylic esters include ethyl acetate, isopropyl acetate, and the like. The amides include formamide, N,N-dimethylformamide, N,N-dimethylacetamide, N-methyl-2-pyrrolidinone, hexamethylphosphorotriamide, and the like. The sulfoxides include dimethyl sulfoxide, sulfolane, and the like. The lower alcohols include methanol, ethanol, propanol, isopropanol, butanol, isobutanol, tert-butanol, and the like. The solvent used in Step 1 is preferably a lower alcohol, more preferably propanol, isopropanol, butanol, isobutanol, or tert-butanol, and particularly preferably isopropanol.

The base used in Step 1 may be any one of inorganic bases and organic bases. Examples of the inorganic bases include alkali metal carbonates, alkali metal hydrogen carbonates, alkali metal hydroxides, and alkali metal hydrides. Here, the alkali metal carbonates include sodium carbonate, potassium carbonate, cesium carbonate, lithium carbonate, and the like. The alkali metal hydrogen carbonates include sodium hydrogen carbonate, potassium hydrogen carbonate, lithium hydrogen carbonate, and the like. The alkali metal hydroxides include sodium hydroxide, potassium hydroxide, barium hydroxide, lithium hydroxide, and the like. The alkali metal hydrides include lithium hydride, sodium hydride, potassium hydride, and the like. Meanwhile, examples of the organic bases include alkali metal alkoxides such as sodium methoxide, sodium ethoxide, potassium methoxide, potassium ethoxide, potassium t-butoxide, and lithium methoxide, N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), N,N,N',N',N'',N''-hexamethylphosphoric triamide (HMPA), and the like. The base used in Step 1 is preferably an organic base, and is particularly preferably triethylamine.

In Step 1, the base is used in an amount of, for example, 1 mole equivalent or more, preferably 1 to 5 mole equivalents, and particularly preferably 2 to 4 mole equivalents relative to compound (4).

The reaction temperature in Step 1 varies depending on the raw material compounds and the reaction reagent, and the reaction is conducted at, for example, 0° C. to 100° C., and preferably 0° C. to 50° C. The reaction time in Step 1 varies depending on the reaction temperature, the raw material compounds, the reaction reagent, and/or the type of the solvent used, and is generally 1 minute to 48 hours, and preferably 1 hour to 18 hours.

After that, the resultant compound (6) may be obtained as a liquid as follows. Specifically, the solvent is removed under reduced pressure or by other means, followed by extraction, washing, and phase-separation using an acid, ethyl acetate, water, and the like, and then by drying.

<Step 2>

Compound (2) can be produced from compound (6). Note that compound (6) can be produced according to <Step 1> described above.

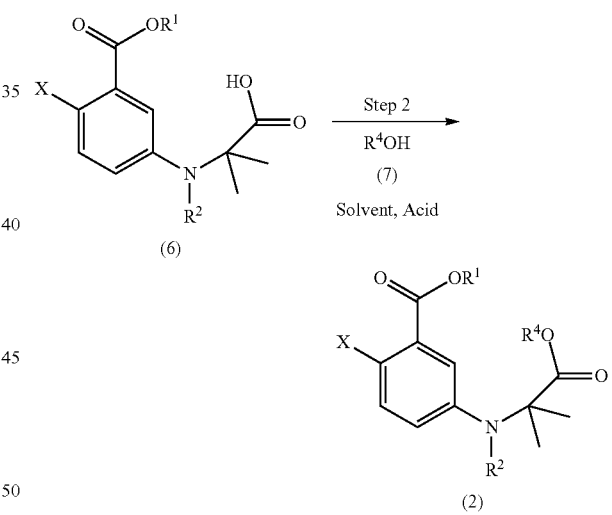

In formulae (2) and (6), the definitions of $R^1$, $R^2$, and X may be the same as those described in Step 1 above. Specifically, $R^1$ represents a hydrogen atom, an optionally substituted alkyl group, an optionally substituted cycloalkyl group, or an optionally substituted aryl group, and is preferably a hydrogen atom or an optionally substituted alkyl group, and more preferably a hydrogen atom. $R^2$ represents a hydrogen atom, an optionally substituted alkyl group, a hydroxy group, or a nitrogen atom-protecting group, and is preferably a hydrogen atom or a nitrogen atom-protecting group, and more preferably a hydrogen atom. X represents a hydroxy group or a leaving group, and is preferably a leaving group, more preferably a halogen atom, and further preferably a bromine atom. In formulae (2) and (7), $R^4$ represents an optionally substituted alkyl group, an optionally substituted cycloalkyl group, or an optionally substituted aryl group. R⁴ is preferably an optionally substituted alkyl group, more preferably a $C_{1-12}$ alkyl group, further preferably a $C_{1-8}$ alkyl group, especially preferably a methyl group, an ethyl group, a n-propyl group, an isopropyl group, a n-butyl group, an isobutyl group, a sec-butyl group, or a tert-butyl group, and particularly preferably a methyl group.

The solvent used in Step 2 is not particularly limited, as long as the solvent does not inhibit the reaction and can dissolve the starting substance to some degree. Preferred examples of the solvent include aromatic hydrocarbons, halogenated hydrocarbons, ethers, lower-alkylcarboxylic esters, amides, sulfoxides, lower alcohols, water, and mixture solvents thereof. The aromatic hydrocarbons include benzene, toluene, xylene, and the like. The halogenated hydrocarbons include dichloromethane, chloroform, carbon tetrachloride, dichloroethane, chlorobenzene, dichlorobenzene, and the like. The ethers include diethyl ether, diisopropyl ether, tetrahydrofuran, cyclopentyl methyl ether, methyl tert-butyl ether, dioxane, dimethoxyethane, diethylene glycol dimethyl ether, and the like. The lower-alkylcarboxylic esters include ethyl acetate, isopropyl acetate, and the like. The amides include formamide, N,N-dimethylformamide, N,N-dimethylacetamide, N-methyl-2-pyrrolidinone, hexamethylphosphorotriamide, and the like. The sulfoxides include dimethyl sulfoxide, sulfolane, and the like. The lower alcohols include methanol, ethanol, propanol, isopropanol, butanol, isobutanol, tert-butanol, anhydrous ones of these alcohols, and the like. The solvent used in Step 2 is preferably a lower alcohol, more preferably methanol, ethanol, propanol, or an anhydrous one of these alcohols, and further preferably methanol. In addition, the above-described compound of formula (7) may also serve as a solvent.

The reaction temperature in Step 2 varies depending on the raw material compound and the reaction reagent, and the reaction is conducted at, for example, 0° C. to 100° C., and preferably 0° C. to 80° C. The reaction time in Step 2 varies depending on the reaction temperature, the raw material compound, the reaction reagent, and/or the type of the solvent used, and is generally 1 minute to 48 hours, and preferably 1 hour to 24 hours.

Step 2 is preferably conducted in the presence of an acid. Examples of usable acids include inorganic acids such as hydrochloric acid, sulfuric acid, nitric acid, phosphoric acid, hydrogen bromide, and hydrofluoric acid; organic acids such as trifluoroacetic acid, methanesulfonic acid, trifluoromethanesulfonic acid, benzenesulfonic acid, p-toluenesulfonic acid, and aminosulfonic acid; Lewis acids such as boron tribromide, boron trichloride, boron trifluoride, and aluminum chloride; and the like.

After that, the resultant compound (2) may be obtained as a liquid as follows. Specifically, the solvent is removed under reduced pressure or by other means, followed by extraction, washing, and phase-separation using ethyl acetate, water, saturated aqueous sodium chloride, and the like, and then by drying.

Moreover, the obtained compound (2) may be purified by column chromatography or the like. As a packing material for the column chromatography, for example, silica gel, alumina, or the like can be used.

<Step 3>

Compound (2) can be obtained by using a compound (compound (5)') of formula (5)' instead of the compound of formula (5) used in Step 1 and by reacting compound (5)' with compound (4) in the same manner as in Step 1. In formula (5)', R⁴ represents an optionally substituted alkyl group, an optionally substituted cycloalkyl group, or an optionally substituted aryl group. R⁴ is preferably an optionally substituted alkyl group, more preferably a $C_{1-12}$ alkyl group, further preferably a $C_{1-8}$ alkyl group, especially preferably a methyl group, an ethyl group, a n-propyl group, an isopropyl group, a n-butyl group, an isobutyl group, a sec-butyl group, or a tert-butyl group, and particularly preferably a methyl group. In formula (5)', Y represents a hydroxy group or a leaving group, and is preferably a leaving group, more preferably a halogen atom, and further preferably a bromine atom. The definitions of the other substituents, the solvent and base used, and the reaction conditions including the reaction temperature and the reaction time are the same as those in Step 1.

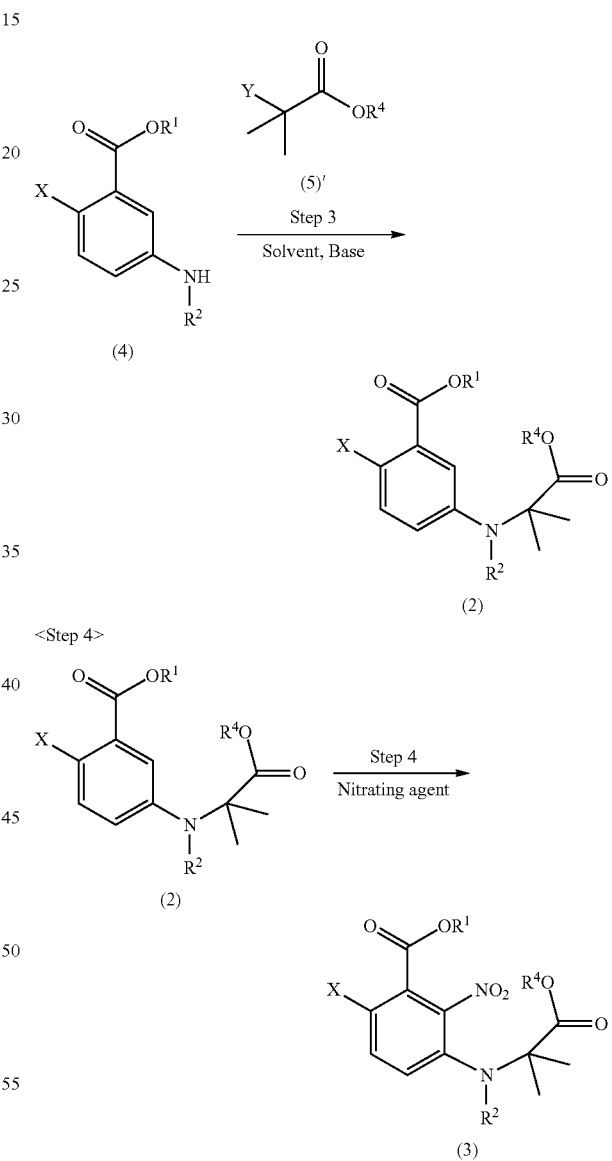

Step 4 is a step of producing compound (3) by reacting compound (2) with a nitrating agent to conduct nitration of the benzene ring of compound (2) at the 2-position.

The definitions of R¹, R², R⁴, and X in formulae (2) and (3) are the same as those of R¹, R², R⁴, and X described in <Step 1> and <Step 2> above.

Examples of the nitrating agent used in Step 4 include 60 to 100% nitric acid, alkali metal nitrates, nitric acid alkyl esters, nitronium tetrafluoroborate (NO$_2$BF$_4$), nitronium trifluoromethanesulfonate (NO$_2$CF$_3$SO$_3$), and the like. The alkali metal nitrates include sodium nitrate, potassium nitrate, and the like, and the nitric acid alkyl esters include ethyl nitrate, amyl nitrate, and the like. Nitrating agents preferably used in Step 4 include 60 to 100% nitric acid and alkali metal nitrates such as sodium nitrate and potassium nitrate, and the nitrating agent is more preferably an alkali metal nitrate such as sodium nitrate or potassium nitrate, and particularly preferably sodium nitrate.

The nitrating agent is used in an amount of, for example, 1 mole equivalent or more, preferably 1 to 10 mole equivalents, and particularly preferably 1 to 1.5 mole equivalents relative to compound (2).

This reaction may be conducted without using a solvent. In general, however, sulfuric acid, acetic acid, acetic anhydride, trifluoroacetic acid, trifluoromethanesulfonic acid, or the like is used as the solvent. In some cases, a mixture of any ones of these solvents may be used. Solvents usable in this step include the solvents listed in Steps 1 and 2 above.

The reaction temperature in Step 4 varies depending on the raw material compound and the reaction reagent, and is, for example, −50° C. to 100° C., and preferably 25° C. to 60° C. The reaction time in Step 4 varies depending on the reaction temperature, the raw material compound, the reaction reagent, and/or the type of the solvent used, and is generally 1 minute to 48 hours, and preferably 5 minute to 24 hours.

After that, the obtained compound (3) may be obtained as a solid as follows. Specifically, the solvent is removed under reduced pressure or by other means, followed by extraction, washing, and phase-separation using ethyl acetate, water, aqueous sodium hydroxide solution, and saturated aqueous sodium chloride, and then by drying.

In necessary, the obtained compound (3) can be purified by an ordinary method such as washing with a solvent, recrystallization, or reprecipitation. Solvents usable for the purification include the solvents listed in Steps 1 and 2 above.

<Step 5>

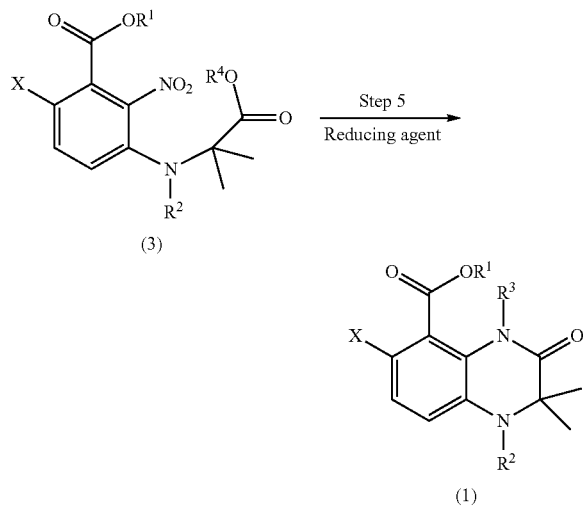

Step 5 is a step of producing the target compound (1) by reducing the nitro group of compound (3) in the presence of a reducing agent, followed by cyclization.

In formulae (1) and (3), the definitions of R$^1$, R$^2$, and X are the same as those of R$^1$, R$^2$, and X described in <Step 1> above. In formula (3), the definition of R$^4$ is the same as that of R$^4$ described in <Step 2> above. In formula (1), R$^3$ represents a hydrogen atom, an optionally substituted alkyl group, a hydroxy group, or a nitrogen atom-protecting group, and preferably represents a hydrogen atom.

Examples of the reducing agent used in Step 5 include reducing metals, reducing metal salts, sodium dithionite, and sodium sulfide. The reducing metals include iron, zinc, tin, magnesium, indium, and the like, and the reducing metal salts include tin dichloride, titanium trichloride, and the like.

When the reduction is conducted by using a reducing metal or a reducing metal salt, one of these reducing metals or reducing metal salts can be used alone, or a combination thereof can be used. The reducing agent is preferably a reducing metal, and more preferably iron powder. The amount of the reducing agent used may be, for example, in a range from 0.5 to 5 mole equivalents, and preferably in a range from 1 to 3 mole equivalents relative to compound (3).

In addition, as an additive, an acid such as hydrochloric acid, sulfuric acid, or acetic acid, or an alkali such as sodium hydroxide, sodium hydrogen sulfite, ammonium chloride, ammonium sulfide, or ammonia water can be used. The amount of the additive used may be, for example, in a range from 0.5 to 50 mole equivalents, and preferably in a range from 1 to 40 mole equivalents relative to compound (3), although the amount depends on the type of the additive.

Compound (1) can also be produced by a catalytic reduction method using a hydrogenation catalyst. Specifically, compound (1) can be obtained by using compound (3) as a raw material and reacting compound (3) in the presence of a hydrogenation catalyst in a solvent under a hydrogen atmosphere.

Specific examples of the hydrogenation catalyst used for the catalytic reduction method include palladium catalysts, platinum catalysts, nickel catalysts, rhodium catalysts, ruthenium catalysts, osmium catalysts, and the like. Specific examples thereof include palladium-carbon, palladium-black, palladium carbon-ethylenediamine complex, palladium-fibroin, palladium hydroxide-carbon, palladium hydroxide, palladium oxide, platinum oxide, platinum-carbon, platinum-black, Raney nickel, rhodium-carbon, rhodium-alumina, ruthenium-carbon, osmium-carbon, Lindlar catalysts, and the like. The amount of the hydrogenation catalyst used is generally 0.01% by mass to 20% by mass relative to compound (3), where compound (3) is taken as 100% by mass. The amount of the hydrogenation catalyst is preferably 0.5% by mass to 10% by mass. For conducting such hydrogenation, a poisoning agent such as dimethyl sulfoxide or ethylenediamine can be added to reduce the catalytic activity. The amount of the poisoning agent used may be, for example, in a range from 1 to 5 mole equivalents, and is preferably in a range from 2 to 3 mole equivalents relative to compound (3).

The reaction of Step 5 can be conducted with or without using a solvent. As the solvent, any of the solvents listed in Steps 1 and 2 above can be used. Specific examples of the solvent usable in Step 5 include ether-based solvents such as diethyl ether and tetrahydrofuran, halogenated hydrocarbon-based solvents such as dichloromethane and chloroform, aromatic hydrocarbon-based solvents such as toluene and benzene, ester-based solvents such as ethyl acetate and isopropyl acetate, aprotic polar solvents such as dimethylformamide and dimethyl sulfoxide, alcohol-based solvents such as methanol and isopropanol, water, and the like. One of these solvents is used alone, or two or more thereof are used as a mixture.

The reaction temperature in Step 5 varies depending on the raw material compound and the reaction reagent, and the reaction is conducted at, for example, −78° C. to 200° C., preferably −20° C. to 100° C., and particularly preferably −5° C. to 50° C. The reaction time in Step 5 varies depending on the reaction temperature, the raw material compound, the reaction reagent, and/or the type of the solvent used, and is generally 1 minute to 48 hours, and is preferably 5 minutes to 24 hours.

After that, the resultant compound (1) may be obtained as a solid as follows. Specifically, the solvent is removed under reduced pressure or by other means, and ethyl acetate or the like is added thereto, followed by stirring. Then, the insoluble matter is removed by filtration, and then the filtrate is subjected to concentration, washing, drying, and the like.

[Production Method 2]

Compound (1) can also be produced from compound (3) through compound (X) having an amino group (—NH$_2$).

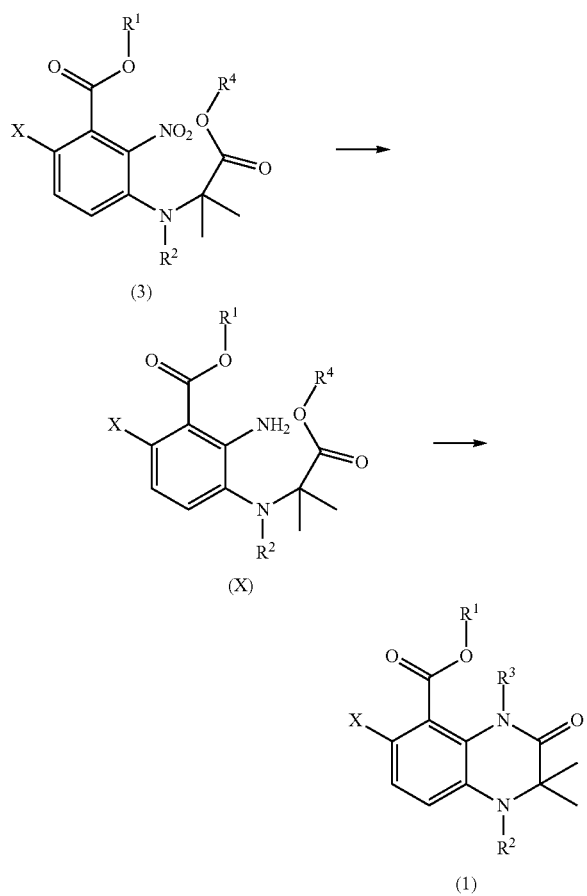

Specifically, compound (X) is produced by reducing the nitro group of compound (3) in the presence of a reducing agent, followed by cyclization. In this manner, the target compound (1) can be produced.

In formulae (1), (3), and (X), the definitions of R$^1$, R$^2$, and X are the same as those of R$^1$, R$^2$, and X described in <Step 1> above. In formulae (3) and (X), the definition of R$^4$ is the same as that of R$^4$ described in <Step 2> above. In formula (1), R$^3$ represents a hydrogen atom, an optionally substituted alkyl group, a hydroxy group, or a nitrogen atom-protecting group, and preferably a hydrogen atom or a nitrogen atom-protecting group, and more preferably a hydrogen atom.

Further, compound (1) can also be produced by [Production Method 3] below by using compound (9) as a raw material.

Figure 3:
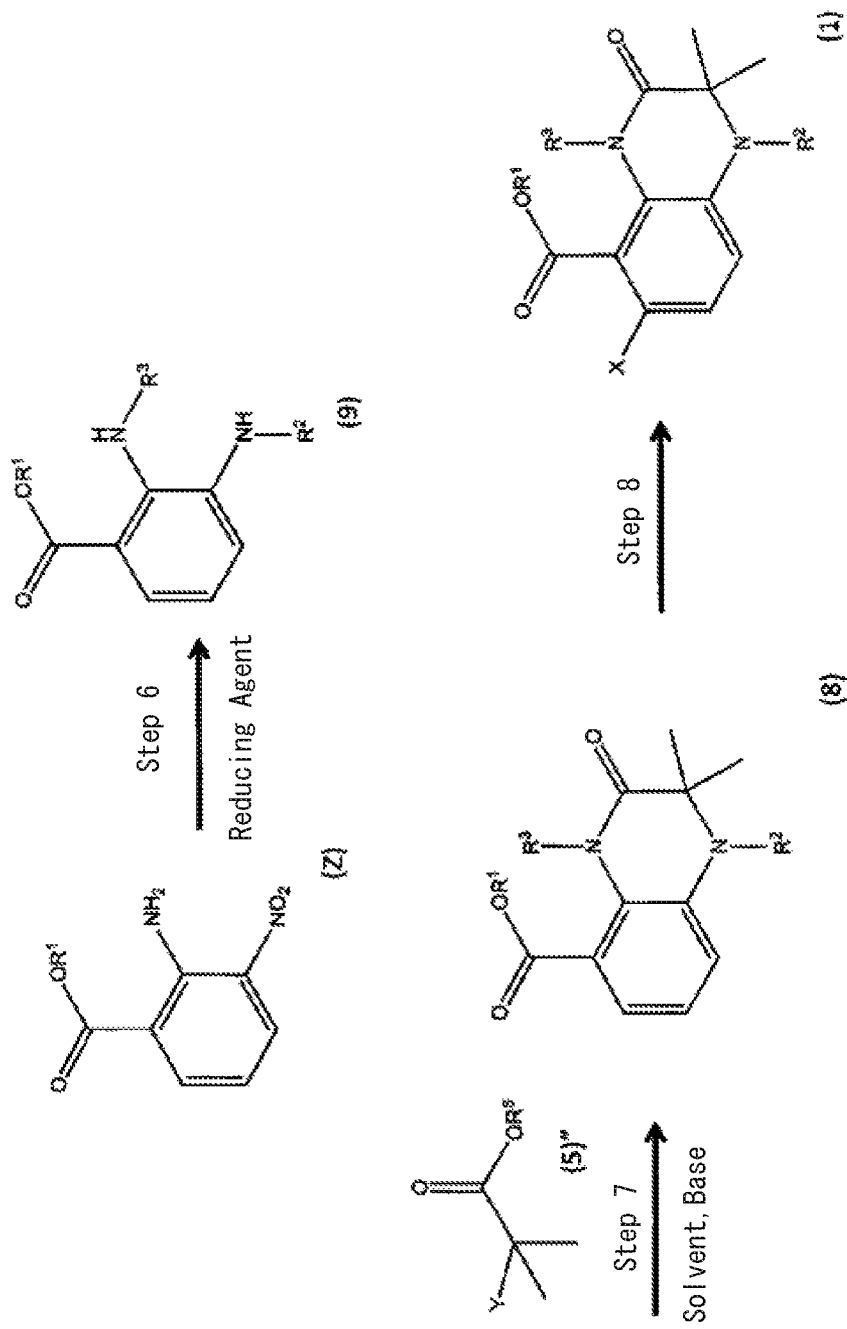
FIG. 3 shows production steps in Method 3 for producing compound (1).

[Production Method 3] (see FIG. 3)

<Step 6>

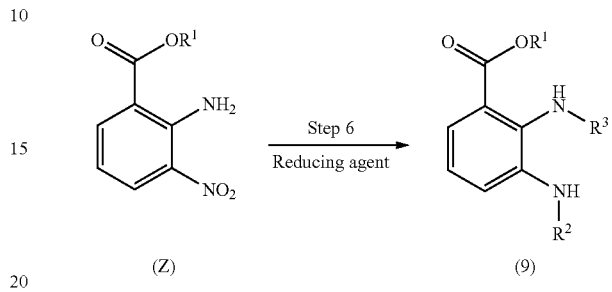

As compound (9) serving as a raw material, one that is commercially available or produced by a known method can be used, and, for example, compound (9) can be produced by Step 6 shown above.

Step 6 is a step of producing compound (9) by reducing the nitro group of compound (Z) in the presence of a reducing agent.

In formulae (Z) and (9), R$^1$ represents a hydrogen atom, an optionally substituted alkyl group, an optionally substituted cycloalkyl group, or an optionally substituted aryl group, and is preferably a hydrogen atom or an optionally substituted alkyl group, and more preferably a hydrogen atom. In formula (9), R$^2$ represents a hydrogen atom, an optionally substituted alkyl group, a hydroxy group, or a nitrogen atom-protecting group, and is preferably a hydrogen atom or a nitrogen atom-protecting group, and more preferably a hydrogen atom. In formula (9), R$^3$ represents a hydrogen atom, an optionally substituted alkyl group, a hydroxy group, or a nitrogen atom-protecting group, and is a hydrogen atom or a nitrogen atom-protecting group, and more preferably a hydrogen atom.

Examples of the reducing agent used in Step 6 include reducing metals, reducing metal salts, sodium dithionite, and sodium sulfide. The reducing metals include iron, zinc, tin, magnesium, indium, and the like, and the reducing metal salts include tin dichloride, titanium trichloride, and the like.

When the reduction is conducted by using a reducing metal or a reducing metal salt, one of these reducing metals or reducing metal salts can be used alone, or a combination thereof can be used. The reducing agent is preferably a reducing metal, and more preferably zinc powder. The amount of the reducing agent used may be, for example, in a range from 0.5 to 20 mole equivalents, and is preferably in a range from 1 to 15 mole equivalents relative to compound (Z).

In addition, as an additive, an acid such as hydrochloric acid, sulfuric acid, or acetic acid, or an alkali such as sodium hydroxide, sodium hydrogen sulfite, ammonium chloride, ammonium sulfide, or ammonia water can be used. The amount of the additive used may be, for example, in a range from 0.5 to 50 mole equivalents, and is preferably in a range from 1 to 40 mole equivalents relative to compound (Z), although the amount varies depending on the type of the additive.

Compound (9) can also be produced by a catalytic reduction method using a hydrogenation catalyst. Specifically, compound (9) can be obtained by using compound (Z) as a raw material, and reacting compound (Z) in the presence of a hydrogenation catalyst in a solvent under a hydrogen atmosphere.

Specific examples of the hydrogenation catalyst used in the catalytic reduction method include palladium catalysts, platinum catalysts, nickel catalysts, rhodium catalysts, ruthenium catalysts, osmium catalysts, and the like. Specific examples include palladium-carbon, palladium-black, palladium carbon-ethylenediamine complex, palladium-fibroin, palladium hydroxide-carbon, palladium hydroxide, palladium oxide, platinum oxide, platinum-carbon, platinum-black, Raney nickel, rhodium-carbon, rhodium-alumina, ruthenium-carbon, osmium-carbon, Lindlar catalysts, and the like. The amount of the hydrogenation catalyst used is generally 0.01% by mass to 20% by mass relative to compound (Z), where compound (Z) is taken as 100% by mass. The amount of the hydrogenation catalyst is preferably 0.5% by mass to 10% by mass. For conducting such hydrogenation, a poisoning agent such as dimethyl sulfoxide or ethylenediamine can be added to reduce the catalytic activity. The amount of the poisoning agent used may be, for example, in a range from 1 to 5 mole equivalents, and is preferably in a range from 2 to 3 mole equivalents relative to compound (Z).

The reaction of Step 6 can be conducted with or without using a solvent. As the solvent, any of the solvents listed in Steps 1 and 2 above can be used. Specific examples of the solvent usable in Step 6 include ether-based solvents such as diethyl ether and tetrahydrofuran, halogenated hydrocarbon-based solvents such as dichloromethane and chloroform, aromatic hydrocarbon-based solvents such as toluene and benzene, ester-based solvents such as ethyl acetate and isopropyl acetate, aprotic polar solvents such as dimethylformamide and dimethyl sulfoxide, alcohol-based solvents such as methanol and isopropanol, water, and the like. One of these solvents is used alone, or two or more thereof are used as a mixture.

The reaction temperature in Step 6 varies depending on the raw material compound and the reaction reagent, and the reaction is conducted at, for example, −78° C. to 200° C., preferably −20° C. to 100° C., and particularly preferably −5° C. to 50° C. The reaction time in Step 6 varies depending on the reaction temperature, the raw material compound, the reaction reagent, and/or the type of the solvent used, and is generally 1 minute to 48 hours, and preferably 5 minutes to 24 hours.

After that, the resultant compound (1) may be obtained as a solid as follows. Specifically, the zinc powder and the like are removed by filtration, and the solvent is removed under reduced pressure or by other means, followed by extraction, washing, and phase-separation using ethyl acetate, saturated aqueous sodium hydrogen carbonate, water, saturated aqueous sodium chloride, and the like, and then by drying.

<Step 7>

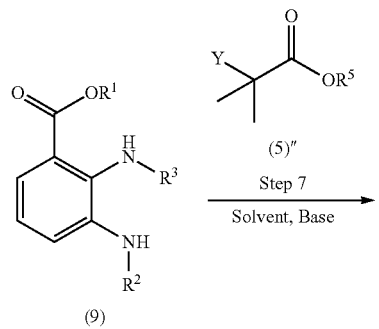

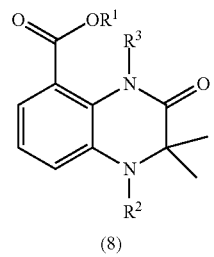

Step 7 is a step of producing compound (8) by reacting compound (9) with compound (5)″ in a solvent in the presence of a base.

In formula (5)″, $R^5$ represents a hydrogen atom, an optionally substituted alkyl group, an optionally substituted cycloalkyl group, or an optionally substituted aryl group. $R^5$ is preferably a hydrogen atom or an optionally substituted alkyl group, more preferably a hydrogen atom or a $C_1$-12 alkyl group, further preferably a hydrogen atom or a $C_1$-8 alkyl group, especially preferably a hydrogen atom, a methyl group, an ethyl group, a n-propyl group, an isopropyl group, a n-butyl group, an isobutyl group, a sec-butyl group, or a tert-butyl group, and particularly preferably a hydrogen atom, a methyl group, or an ethyl group. Y represents a hydroxy group or a leaving group, and is preferably a leaving group, more preferably a halogen atom, and further preferably a bromine atom. In formulae (8) and (9), $R^1$, $R^2$, and $R^3$ may be the same as those defined in Step 6 above. Specifically, $R^1$ represents a hydrogen atom, an optionally substituted alkyl group, an optionally substituted cycloalkyl group, or an optionally substituted aryl group, and is preferably a hydrogen atom or an optionally substituted alkyl group, and more preferably a hydrogen atom. $R^2$ represents a hydrogen atom, an optionally substituted alkyl group, a hydroxy group, or a nitrogen atom-protecting group, and is preferably a hydrogen atom or a nitrogen atom-protecting group, and more preferably a hydrogen atom. $R^3$ represents a hydrogen atom, an optionally substituted alkyl group, a hydroxy group, or a nitrogen atom-protecting group, preferably a hydrogen atom or a nitrogen atom-protecting group, and more preferably a hydrogen atom.

Compound (5)″ is used in an amount of, for example, 1 mole equivalent or more, preferably 1 to 2 mole equivalents, and particularly preferably 1 to 1.2 mole equivalents relative to compound (9).

The base used in this step may be any one of inorganic bases and organic bases. Examples of the inorganic bases include alkali metal carbonates, alkali metal hydrogen carbonates, alkali metal hydroxides, and alkali metal hydrides. The alkali metal carbonates include sodium carbonate, potassium carbonate, cesium carbonate, lithium carbonate, and the like, and the alkali metal hydrogen carbonates include sodium hydrogen carbonate, potassium hydrogen carbonate, lithium hydrogen carbonate, and the like. The alkali metal hydroxides include sodium hydroxide, potassium hydroxide, barium hydroxide, lithium hydroxide, and the like, and the alkali metal hydrides include lithium hydride, sodium hydride, potassium hydride, and the like. Examples of the organic bases include alkali metal alkoxides such as sodium methoxide, sodium ethoxide, potassium methoxide, potassium ethoxide, potassium t-butoxide, and lithium methoxide, N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di (t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), N,N,N',N',N'',N''-hexamethylphosphoric triamide (HMPA), and the like. The base used in this step is preferably an organic bases, and particularly preferably triethylamine.

In Step 7, the base is used in an amount of 1 mole equivalents or more, preferably 1 to 5 mole equivalents, and particularly preferably 2 to 4 mole equivalents relative to compound (9).

The solvent used in Step 7 is not particularly limited, as long as the solvent does not inhibit the reaction and can dissolve the starting substance to some degree. Examples of the solvent include aromatic hydrocarbons, halogenated hydrocarbons, ethers, lower-alkylcarboxylic esters, amides, sulfoxides, lower alcohols, water, and mixture solvents thereof. The aromatic hydrocarbons include benzene, toluene, xylene, and the like. The halogenated hydrocarbons include dichloromethane, chloroform, carbon tetrachloride, dichloroethane, chlorobenzene, dichlorobenzene, and the like. The ethers include diethyl ether, diisopropyl ether, tetrahydrofuran, cyclopentyl methyl ether, methyl tert-butyl ether, dioxane, dimethoxyethane, diethylene glycol dimethyl ether, and the like. The lower-alkylcarboxylic esters include ethyl acetate, isopropyl acetate, and the like. The amides include formamide, N,N-dimethylformamide, N,N-dimethylacetamide, N-methyl-2-pyrrolidinone, hexamethylphosphorotriamide, and the like. The sulfoxides include dimethyl sulfoxide, sulfolane, and the like. The lower alcohols include methanol, ethanol, propanol, isopropanol, butanol, isobutanol, tert-butanol, and the like. The solvent used in this step is preferably a lower alcohol, and particularly preferably 1-propanol.

In addition, compound (5)'' may be used also as the solvent in Step 7.

After that, the resultant compound (8) may be obtained as a solid as follows. Specifically, the solvent is removed under reduced pressure or by other means, followed by extraction, washing, and phase-separation using ethyl acetate, water, and saturated aqueous sodium chloride, and then by drying.

Further, the obtained compound (8) may be purified by column chromatography or the like. As a packing material for the column chromatography, for example, silica gel, alumina, or the like can be used.

The reaction temperature in Step 7 varies depending on the raw material compounds and the reaction reagent, and the reaction is conducted at, for example, 0° C. to 200° C., and preferably 25° C. to 150° C. The reaction time in Step 7 varies depending on the reaction temperature, the raw material compounds, the reaction reagent, and/or the type of the solvent used, and is generally 1 minute to 48 hours, and preferably 1 hour to 18 hours.

<Step 8>

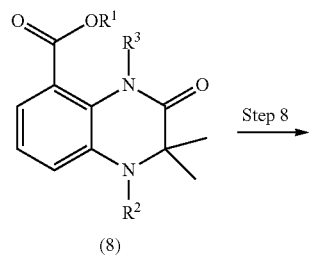

(8)

Step 8

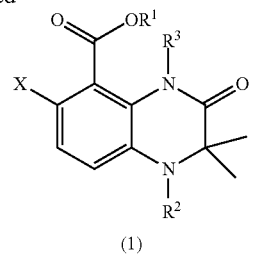

(1)

Step 8 is a step of producing compound (1) by introducing X to the 7-position of compound (8).

Here, X represents a hydroxy group or a leaving group, and is preferably a leaving group, more preferably a halogen atom, and further preferably a bromine atom. In formulae (1) and (8), the definitions of $R^1$, $R^2$, and $R^3$ are the same as those of $R^1$, $R^2$, and $R^3$ described in <Step 7> above.

When X is a hydroxy group, the hydroxy group can be introduced to the 7-position of compound (8) by using any of various oxidizing agents or the like. Here, as the oxidizing agents, various oxidizing agents listed in COMPREHENSIVE ORGANIC TRANSFORMATIONS, A Guide to Functional Group Preparations, Richard C. Larock, 1989, pp 485-486 can be used. When X is a hydroxy group or a leaving group, especially, a halogen atom, the target compound (1) can be produced, for example, by reacting compound (8) with the halogenating agent in the presence or absence of an acid such as concentrated sulfuric acid, hydrochloric acid, methanesulfonic acid, toluenesulfonic acid, trifluoromethanesulfonic acid, camphorsulfonic acid, trifluoroacetic acid, acetic acid, aluminum chloride, iron(III) chloride, titanium tetrachloride, or titanium tetraisopropoxide.

Examples of the halogenating agent include chlorine, bromine, 1,3-dibromo-5,5-dimethylhydantoin, N-chlorosuccinimide, N-bromosuccinimide, tetrabutylammonium tribromide, dimethylaminopyridine tribromide, 2,4,4,6-tetrabromo-2,5-cyclohexadienone, and the like. The halogenating agent is particularly preferably N-bromosuccinimide or 2,4,4,6-tetrabromo-2,5-cyclohexadienone.

The halogenating agent is used in an amount of 1 mole equivalent or more, preferably 1 to 2 mole equivalents, and particularly preferably 1 to 1.5 mole equivalents relative to compound (8).

The solvent used in this step is not particularly limited, as long as the solvent does not inhibit the reaction and can dissolve the starting substance to some degree. Examples thereof include aromatic hydrocarbons, halogenated hydrocarbons, ethers, lower-alkylcarboxylic esters, amides, sulfoxides, lower alcohols, water, and mixture solvents thereof. The aromatic hydrocarbons include benzene, toluene, xylene, and the like. The halogenated hydrocarbons include dichloromethane, chloroform, carbon tetrachloride, dichloroethane, chlorobenzene, dichlorobenzene, and the like. The ethers include diethyl ether, diisopropyl ether, tetrahydrofuran, cyclopentyl methyl ether, methyl tert-butyl ether, dioxane, dimethoxyethane, diethylene glycol dimethyl ether, and the like. The lower-alkylcarboxylic esters include ethyl acetate, isopropyl acetate, and the like. The amides include formamide, N,N-dimethylformamide, N,N-dimethylacetamide, N-methyl-2-pyrrolidinone, hexamethylphosphorotriamide, and the like. The sulfoxides include dimethyl sulfoxide, sulfolane, and the like. The lower alcohols include methanol, ethanol, propanol, isopropanol, butanol, isobutanol, tert-butanol, and the like. The solvent used in this step is preferably an amide, and particularly preferably N,N-dimethylformamide. The solvent is more preferably selected from the solvents used in Step 7.

After that, the resultant compound (1) can be obtained as a solid as follows. Specifically, the solvent is removed under reduced pressure or by other means, followed by extraction, washing, and phase-separation using ethyl acetate, water, and saturated aqueous sodium chloride, and then by drying.

Further, the obtained compound (1) may be purified by column chromatography or the like. As a packing material for the column chromatography, for example, silica gel, alumina, or the like can be used.

The reaction temperature in Step 8 varies depending on the raw material compound and the reaction reagent, and the reaction is conducted at, for example, 0° C. to 100° C., and preferably 0° C. to 50° C.

The reaction time in Step 8 varies depending on the reaction temperature, the raw material compound, the reaction reagent, and/or the type of the solvent used, and is generally 1 minute to 48 hours, and preferably 30 minutes to 18 hours.

EXAMPLES

Hereinafter, production examples of the present invention are described. Note that these examples are provided for better understanding of the present invention, and the scope of the present invention is not limited to these examples.

Example 1

Production 1 of Methyl 2-Bromo-5-(1-methoxycarbonyl-1-methylethyl)aminobenzoate (2-1)

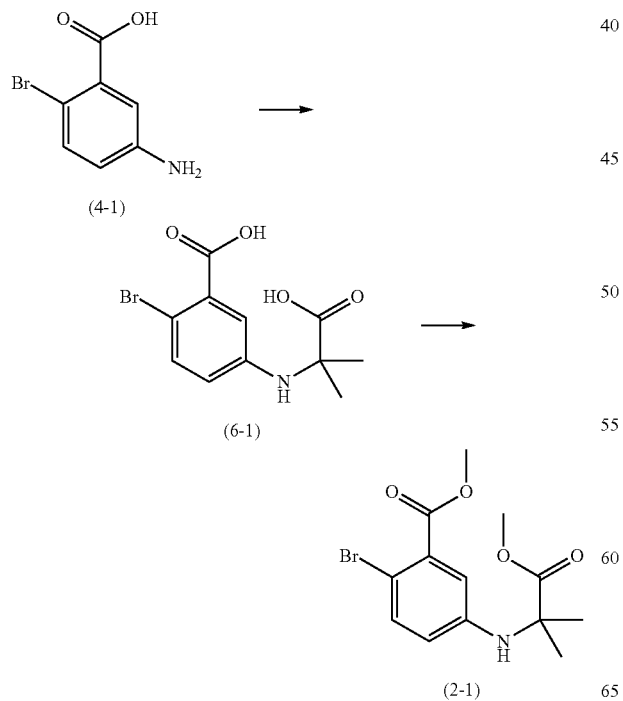

Production of 2-Bromo-5-(1-carboxy-1-methylethyl)aminobenzoic Acid (6-1)

To a mixture of 5-amino-2-bromobenzoic acid (4-1) (10.0 g, 46.3 mmol, commercially available compound) and 2-bromoisobutyric acid (11.6 g, 69.5 mmol, commercially available compound), isopropanol (100 mL) and triethylamine (26 mL, 0.188 mol) were added, followed by stirring at 50° C. for 20 hours. The solvent was removed by evaporation under reduced pressure, and 6 M hydrochloric acid (20 mL), ethyl acetate (500 mL), and water (300 mL) were added, followed by extraction. The organic layer was further washed with water (200 mL) and saturated aqueous sodium chloride (200 mL), and then dried over anhydrous magnesium sulfate. The solvent was removed by evaporation under reduced pressure to obtain the title compound (6-1) (13.7 g, yield: 98%).

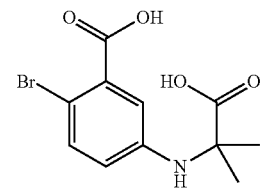

(6-1)

2-Bromo-5-(1-carboxy-1-methylethyl) aminobenzoic Acid
$^1$H-NMR (400 MHz, DMSO-D$_6$) δ:
1.42 (s, 6H), 6.51 (dd, J = 8.8, 2.9 Hz, 1H), 6.87 (d, J = 2.9 Hz, 1H), 7.33 (d, J = 8.8 Hz, 1H), 12.86 (br s, 2H).

Production of Methyl 2-Bromo-5-(1-methoxycarbonyl-1-methylethyl)aminobenzoate (2-1)

To a solution of a mixture of the 2-bromo-5-(1-carboxy-1-methylethyl)aminobenzoic acid (6-1) (10.8 g, 35.8 mmol) obtained in Example 1 above and methanol (7-1) (150 mL), concentrated sulfuric acid (15 mL) was added, followed by heating with stirring for 21.5 hours at an outside temperature of 70° C. The solvent was removed by evaporation under reduced pressure, and ethyl acetate (250 mL) and water (200 mL) were added, followed by extraction. The organic layer was further washed with water (100 mL) and saturated aqueous sodium chloride (100 mL), and then dried over anhydrous magnesium sulfate. The solvent was removed by evaporation under reduced pressure to obtain the title compound (2-1) (9.44 q, yield: 800).

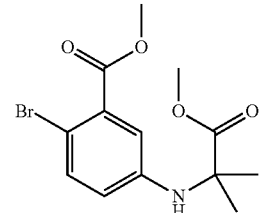

(2-1)

Methyl 2-Bromo-5-(1-methoxycarbonyl-1-m ethylethyl) aminobenzoate
$^1$H-NMR (400 MHz, DMSO-D$_6$) δ:
1.45 (s, 6H), 3.61 (s, 3H), 3.81 (s, 3H), 6.46 (dd, J = 8.8, 2.9 Hz, 1H), 6.51 (s, 1H), 6.85 (d, J = 2.9 Hz, 1H), 7.37 (d, J = 8.8 Hz, 1H).

Example 2

Production 2 of Methyl 2-Bromo-5-(1-methoxycarbonyl-1-methylethyl)aminobenzoate (2-1)

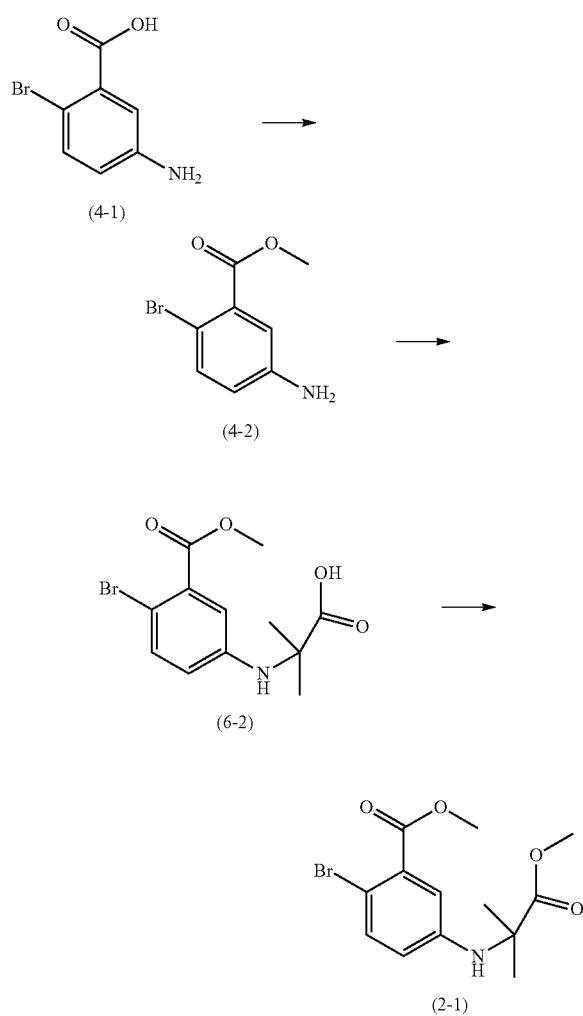

Production of Methyl 5-Amino-2-bromobenzoate (4-2)

To a solution of a mixture of 5-amino-2-bromobenzoic acid (4-1) (2.00 g, 9.26 mmol, commercially available compound) and anhydrous methanol (40 mL), concentrated sulfuric acid (4 mL) was added at room temperature, followed by stirring for 18 hours at an outside temperature of 70° C. The solvent was removed by evaporation under reduced pressure, and a 4 M aqueous sodium hydroxide solution (12 mL) was added, and then ethyl acetate (30 mL) and water (30 mL) were added, followed by extraction. The organic layer was further washed with water (30 mL) and saturated aqueous sodium chloride (30 mL), and then dried over anhydrous magnesium sulfate. The solvent was removed by evaporation under reduced pressure to obtain the title compound (4-2) (0.941 g, yield: 44%).

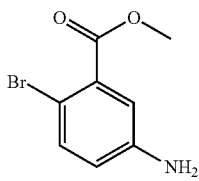

Methyl 5-Amino-2-bromobenzoate
$^1$H-NMR (500 MHz, DMSO-D$_6$) δ:
3.80 (s, 3H), 5.55 (s, 2H), 6.63 (dd, J = 8.6, 2.7 Hz, 1H), 6.95 (d, J = 2.7 Hz, 1H), 7.29 (d, J = 8.6 Hz, 1H).

Production of Methyl 2-Bromo-5-(1-carboxy-1-methylethyl)aminobenzoate (6-2)

To a mixture of the methyl 5-amino-2-bromobenzoate (4-2) (0.941 g, 4.09 mmol) obtained as above, 2-bromoisobutyric acid (1.03 g, 6.17 mmol), and isopropanol (9 mL), triethylamine (2.3 mL, 16.6 mmol) was added, followed by stirring at 50° C. for 16 hours. The solvent was removed by evaporation under reduced pressure, and 2 M hydrochloric acid (10 mL), ethyl acetate (50 mL), and water (50 mL) were added, followed by extraction. The organic layer was further washed with water (50 mL) and saturated aqueous sodium chloride (50 mL), and then dried over anhydrous magnesium sulfate. The solvent was removed by evaporation under reduced pressure to obtain the title compound (6-2) (1.31 g, yield: 100%).

| | |
|---|---|
| Methyl 2-Bromo-5-(1-carboxy-1-methylethyl)aminobenzoate | (6-2) $^1$H-NMR (400 MHz, DMSO-D$_6$) δ: 1.42 (s, 6H), 3.81 (s, 3H), 6.54 (dd, J = 8.8, 3.3 Hz, 1H), 6.88 (d, J = 3.3 Hz, 1H), 7.36 (d, J = 8.8 Hz, 1H), 12.47 (s, 1H). |

Production 1 of Methyl 2-Bromo-5-(1-methoxycarbonyl-1-methylethyl)aminobenzoate (2-1)

To a liquid mixture of the methyl 2-bromo-5-(1-carboxy-1-methylethyl)aminobenzoate (6-2) (0.486 g, 1.54 mmol) obtained as above and anhydrous methanol (9.7 mL), concentrated sulfuric acid (0.97 mL) was added at room temperature, followed by stirring for 23 hours at an outside temperature of 75° C. The solvent was removed by evaporation under reduced pressure, and ethyl acetate (30 mL) and water (30 mL) were added, followed by extraction. The organic layer was further washed with water (30 mL) and saturated aqueous sodium chloride (30 mL), and then dried over anhydrous magnesium sulfate. The solvent was removed by evaporation under reduced pressure. The obtained residue was purified by silica gel column chromatography to obtain the title compound (2-1) (0.256 g, yield: 50%).

Production 2 of Methyl 2-Bromo-5-(1-methoxycarbonyl-1-methylethyl)aminobenzoate (2-1)

To a mixture of the methyl 5-amino-2-bromobenzoate (4-2) (1.00 g, 4.35 mmol) obtained as above, 2-bromoisobutyric acid (1.09 g, 6.52 mmol), and isopropanol (10 mL), triethylamine (2.1 mL, 15.2 mmol) was added, followed by stirring at 50° C. for 21 hours. After the insoluble matter was removed by filtration, the solvent was removed by evaporation under reduced pressure. After methanol (5 mL) was added, the solvent was removed by evaporation under reduced pressure. To the obtained residue, anhydrous methanol (20 mL) and concentrated sulfuric acid (2 mL) were added, followed by stirring for 23 hours at an outside temperature of 70° C. The solvent was removed by evaporation under reduced pressure, and ethyl acetate (20 mL) and water (20 mL) were added, followed by extraction. The organic layer was further washed with a 0.1 M aqueous sodium hydroxide solution (20 mL), water (20 mL), and saturated aqueous sodium chloride (20 mL), and then dried over anhydrous magnesium sulfate. The solvent was removed by evaporation under reduced pressure to obtain the title compound (2-1) (0.971 q, yield: 68%).

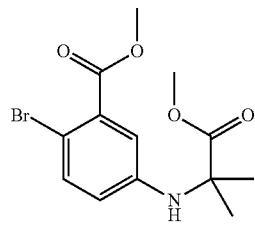

(2-1)

Methyl 2-Bromo-5-(1-methoxycarbonyl-1-methylethyl) aminobenzoate $^1$H-NMR (400 MHz, DMSO-D$_6$) δ:

1.45 (s, 6H), 3.61 (s, 3H), 3.81 (s, 3H), 6.46 (dd, J = 8.8, 2.9 Hz, 1H), 6.51 (s, 1H), 6.85 (d, J = 2.9 Hz, 1H), 7.37 (d, J - 8.8 Hz, 1H).

Example 3

Production of 7-Bromo-8-methoxycarbonyl-3,3-dimethyl-3,4-dihydro-1H-quinoxalin-2-one (1-1)

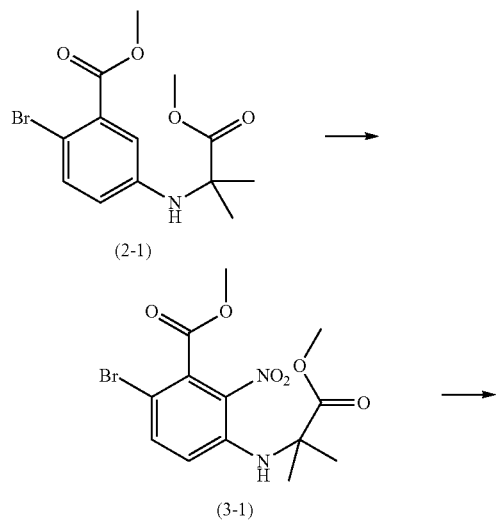

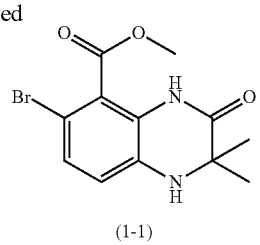

(1-1)

Production of Methyl 6-Bromo-3-(1-methoxycarbonyl-1-methylethyl)amino-2-nitrobenzoate (3-1)

A solution of a mixture of the methyl 2-bromo-5-(1-methoxycarbonyl-1-methylethyl)aminobenzoate (2-1) (2.19 g, 6.63 mmol) obtained in Example 1 or 2 and trifluoroacetic acid (17.5 mL) was stirred at an outside temperature of 50° C., and sodium nitrate (0.567 g, 6.67 mmol) was added, followed by heating with stirring for 17 hours. The solvent was removed by evaporation under reduced pressure, and water (20 mL), a 4 M aqueous sodium hydroxide solution (6 mL), and ethyl acetate (30 mL) were added, followed by extraction. The organic layer was further washed with water (20 mL) and saturated aqueous sodium chloride (20 mL), and then dried over anhydrous magnesium sulfate. The solvent was removed by evaporation under reduced pressure, and then isopropanol (6.6 mL) was added. The crystallized solid was collected by filtration, and the collected material was further washed with isopropanol (3.3 mL) and dried to obtain the title compound (3-1) (0.983 g, yield: 40%).

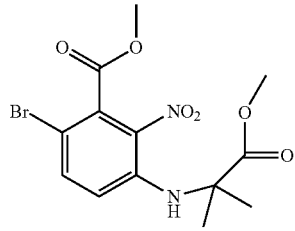

(3-1)

Methyl 6-Bromo-3-(1-methoxycarbonyl-1-methylethyl) amino-2-nitrobenzoate $^1$H-NMR (400 MHz, DMSO-D$_6$) δ:

1.61 (s, 6H), 3.70 (s, 3H), 3.86 (s, 3H), 6.70 (d, J = 9.3 Hz, 1H), 7.76 (d, J = 9.3 Hz, 1H), 8.01 (s, 1H).

Production of 7-Bromo-8-methoxycarbonyl-3,3-dimethyl-3,4-dihydro-1H-quinoxalin-2-one (1-1)

To a solution of a mixture of the methyl 6-bromo-3-(1-methoxycarbonyl-1-methylethyl)amino-2-nitrobenzoate (3-1) (0.702 g, 1.87 mmol) obtained as above, methanol (4.3 mL), and acetic acid (4.3 mL), iron powder (0.319 g, 5.71 mmol) was added under ice-cooling, followed by stirring at room temperature for 18 hours. The solvent was removed by evaporation under reduced pressure, and then ethyl acetate (7 mL) was added, followed by stirring for 3 hours. The insoluble matter was removed by filtration using Celite. The filtrate was concentrated, and the precipitated solid was washed with hexane:ethyl acetate (5:1) (5 mL), and then dried to obtain the title compound (1-1) (0.472 g, yield: 81%).

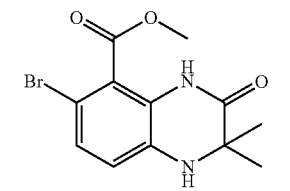

7-Bromo-8-methoxycarbonyl-3, 3-dimethyl-3,
4-dihydro-1H-quinoxalin-2-one $^1$H-NMR (400 MHz, DMSO-D$_6$) δ:
1.22 (s, 6H), 3.84 (s, 3H), 6.46 (s, 1H),
6.72 (d, J = 8.4 Hz, 1H), 7.07 (d, J = 8.4 Hz, 1H),
10.09 (s, 1H).

(1-1)

Example 4

Production of Methyl 2,3-Diaminobenzoate (9-1)

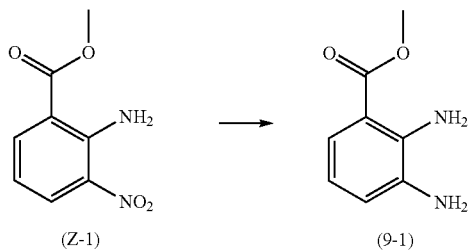

(Z-1) (9-1)

Production of Methyl 2,3-Diaminobenzoate (9-1)

To methyl 2-amino-3-nitrobenzoate (Z-1) (500 mg, 2.78 mmol, commercially available compound), acetic acid (10 mL) was added, followed by heating to 50° C. Then, zinc powder (1.67 g, 25.5 mmol) was added, followed by stirring for 30 minutes. After the reaction liquid was allowed to cool, the zinc powder was removed by filtration, and then the solvent was removed by evaporation under reduced pressure. To the obtained residue, ethyl acetate (15 mL) and saturated aqueous sodium hydrogen carbonate (15 mL) were added, followed by extraction. The organic layer was washed sequentially with water (15 mL) and with saturated aqueous sodium chloride (15 mL), and dried over anhydrous magnesium sulfate. Then, the solvent was removed by evaporation under reduced pressure to obtain the title compound (9-1) (391 mg, yield: 94%).

(9-1)

Methyl
2,3-Diaminobenzoate $^1$H-NMR (400 MHz, CDCl$_3$) δ: 3.87
(s, 3H), 4.54 (br s, 4H), 6.60
(dd, J = 8.2, 7.4 Hz, 1H), 6.85
(dd, J = 7.4, 1.5 Hz, 1H), 7.47
(dd, J = 8.2, 1.5 Hz, 1H).

Example 5

Production of 8-Methoxycarbonyl-3,3-dimethyl-3,4-dihydro-1H-quinoxalin-2-one (8-1)

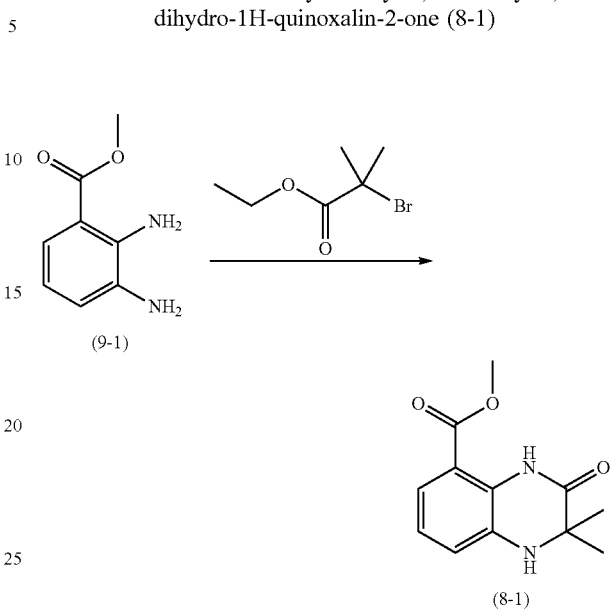

Production 1 of 8-Methoxycarbonyl-3,3-dimethyl-3, 4-dihydro-1H-quinoxalin-2-one (8-1)

To a mixture of the methyl 2,3-diaminobenzoate (9-1) (151 mg, 0.903 mmol) obtained in Example 4 and ethyl 2-bromoisobutyrate (3.0 mL, 20.4 mmol), triethylamine (188 μL, 1.35 mmol) was added, followed by stirring at 100° C. for 2 days. The reaction liquid was allowed to cool, and ethyl acetate (15 mL) and water (15 mL) were added, followed by extraction. The organic layer was washed with saturated aqueous sodium chloride (15 mL), and dried over anhydrous magnesium sulfate. Then, the solvent was removed by evaporation under reduced pressure. The obtained residue was purified by silica gel column chromatography to obtain the title compound (8-1) (82.5 mg, yield: 39%).

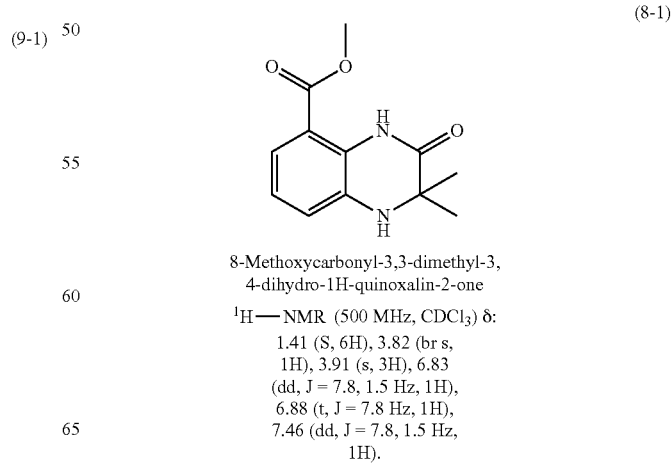

8-Methoxycarbonyl-3,3-dimethyl-3,
4-dihydro-1H-quinoxalin-2-one $^1$H—NMR (500 MHz, CDCl$_3$) δ:
1.41 (S, 6H), 3.82 (br s,
1H), 3.91 (s, 3H), 6.83
(dd, J = 7.8, 1.5 Hz, 1H),
6.88 (t, J = 7.8 Hz, 1H),
7.46 (dd, J = 7.8, 1.5 Hz,
1H).

Example 6

Production of 7-Bromo-8-methoxycarbonyl-3,3-dimethyl-3,4-dihydro-1H-quinoxalin-2-one (1-1)

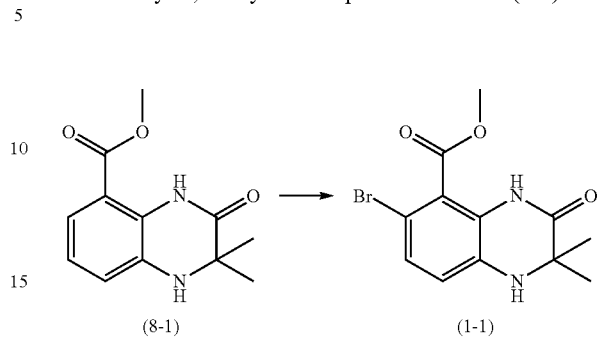

Production 1 of 7-Bromo-8-methoxycarbonyl-3,3-dimethyl-3,4-dihydro-1H-quinoxalin-2-one (1-1)

To the 8-methoxycarbonyl-3,3-dimethyl-3,4-dihydro-1H-quinoxalin-2-one (8-1) (50.2 mg, 0.213 mmol) obtained in Example 5, anhydrous N,N-dimethylformamide (2 mL) and N-bromosuccinimide (37.9 mg, 0.213 mmol) were added, followed by stirring at room temperature for 30 minutes. To the reaction liquid, ethyl acetate (10 mL) and water (10 mL) were added, followed by extraction. The organic layer was washed with saturated aqueous sodium chloride (10 mL), and dried over anhydrous magnesium sulfate. Then, the solvent was removed by evaporation under reduced pressure. The obtained residue was purified by silica gel column chromatography to obtain the title compound (1-1) (26.7 mg, yield: 400).

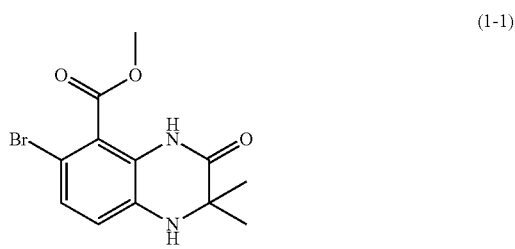

(1-1)

7-Bromo-8-methoxycarbonyl-3,3-dimethyl-3,4-dihydro-1H-quinoxalin-2-one $^1$H-NMR (400 MHz, DMSO-D$_6$) δ:
1.22 (s, 6H), 3.84 (s, 3H), 6.46 (s, 1H), 6.72 (d, J = 8.4 Hz, 1H), 7.07 (d, J = 8.4 Hz, 1H), 10.09 (s, 1H).

Production 2 of 7-Bromo-8-methoxycarbonyl-3,3-dimethyl-3,4-dihydro-1H-quinoxalin-2-one (1-1)

To the 8-methoxycarbonyl-3,3-dimethyl-3,4-dihydro-1H-quinoxalin-2-one (8-1) (50 mg, 0.213 mmol) obtained in Example 5, anhydrous N,N-dimethylformamide (2 mL) was added, followed by cooling to 0° C. Then, 2,4,4,6-tetrabromo-2,5-cyclohexadienone (87.3 mg, 0.213 mmol) was added, followed by stirring at room temperature for 1 hour. To the reaction liquid, ethyl acetate (10 mL) and water (10 mL) were added, followed by extraction. The organic layer

---

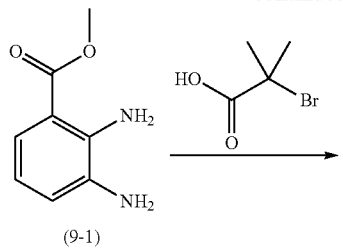

(9-1)

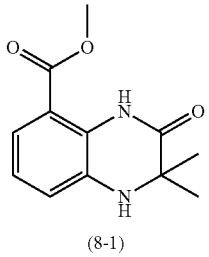

(8-1)

Production 2 of 8-Methoxycarbonyl-3,3-dimethyl-3,4-dihydro-1H-quinoxalin-2-one (8-1)

To a mixture of the methyl 2,3-diaminobenzoate (9-1) (100 mg, 0.602 mmol) obtained in Example 4, 1-propanol (5.0 mL), and 2-bromoisobutyric acid (111 mg, 0.662 mmol), triethylamine (126 μL, 0.903 mmol) was added, followed by stirring at 50° C. for 5 hours. The reaction liquid was allowed to cool, and the solvent was removed by evaporation under reduced pressure. To the obtained residue, ethyl acetate (10 mL) and water (10 mL) were added, followed by extraction. The organic layer was washed with saturated aqueous sodium chloride (10 mL), and dried over anhydrous magnesium sulfate. Then, the solvent was removed by evaporation under reduced pressure. The obtained residue was purified by silica gel column chromatography to obtain the title compound (8-1) (88.7 mg, yield: 63%).

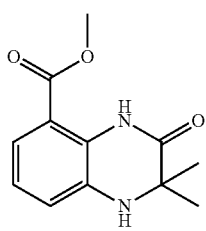

(8-1)

8-Methoxycarbonyl-3,3-dimethyl-3,4-dihydro-1H-quinoxalin-2-one $^1$H-NMR (500 MHz, CDCl$_3$) δ:
1.41 (s, 6H), 3.82 (br s, 1H), 3.91 (s, 3H), 6.83 (dd, J = 7.8, 1.5 Hz, 1H), 6.88 (t, J = 7.8 Hz, 1H), 7.46 (dd, J = 7.8, 1.5 Hz, 1H).

was washed with saturated aqueous sodium chloride (10 mL), and dried over anhydrous magnesium sulfate. Then, the solvent was removed by evaporation under reduced pressure. The obtained residue was purified by silica gel column chromatography to obtain the title compound (1-1) (30.7 mg, yield: 46%).

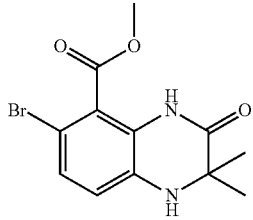

(1-1)

7-Bromo-8-methoxycarbonyl-
3,3-dimethyl-3,4-dihydro-1H-
quinoxalin-2-one
$^1$H-NMR (400 MHz, DMSO-D$_6$) δ:
1.22 (s, 6H), 3.84 (s, 3H), 6.46
(s, 1H), 6.72 (d, J = 8.4 Hz, 1H),
7.07 (d, J = 8.4 Hz, 1H), 10.09 (s, 1H).

INDUSTRIAL APPLICABILITY

According to the present invention, the use of the novel intermediate compound (2) makes it possible to obtain compound (3) and compound (1) highly efficiently without purification by column chromatography. In addition, the reaction of compound (4) with compound (5) or (5) ' makes it possible to efficiently obtain compound (2) in a high yield without using an excessive amount of compound (5) or (5)' in contrast to the above-described prior art (Step 5 in FIG. 1), without using compound (5) or (5)' as the reaction solvent, and without requiring a purification step by column chromatography (see FIG. 2). Moreover, the target compound (1) can be obtained from the raw material compound (4) through three to four steps in total. In addition, the target compound (1) can be obtained through two steps in total by reacting compound (9) with compound (5)" to obtain compound (8), which is a precursor of compound (1), and then by introducing a leaving group to the 7-position of the precursor compound (8) (see FIG. 3).

Compound (1) is useful as an intermediate for producing a 1,2,3,4,-tetrahydroquinoxaline derivative having a binding activity to the glucocorticoid receptor or a salt thereof. Here, the glucocorticoid receptor is a 94 kDa ligand-actived intracellular transcription regulatory factor of the nuclear receptor superfamily. The glucocorticoid receptor is associated with treatment and prevention of metabolic disorders such as diabetes mellitus and obesity, inflammatory diseases such as arthritis, enteritis, and chronic obstructive lung disease, autoimmune diseases, allergic diseases, central nervous system diseases, cardiovascular diseases, homeostasis-related diseases, glaucoma, and the like (Patent Literature 1).

Moreover, it is also possible to provide novel intermediates for producing a 1,2,3,4-tetrahydroquinoxaline derivative having a binding activity to the glucocorticoid receptor.

The invention claimed is:
1. A method for producing a compound represented by formula (1):

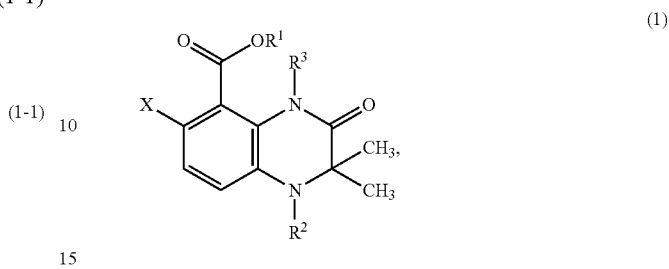

(1)

or a salt thereof,
wherein:
  R$^1$ represents a hydrogen atom, an alkyl group, a cycloalkyl group or an aryl group;
  R$^2$ represents a hydrogen atom, an alkyl group, a hydroxy group or a tert-butoxycarbonyl group;
  R$^3$ represents a hydrogen atom, an alkyl group, a hydroxy group or a tert-butoxycarbonyl group; and
  X represents a hydroxy group or a halogen atom;
the method comprising the steps of:
(i) reacting a compound represented by formula (2):

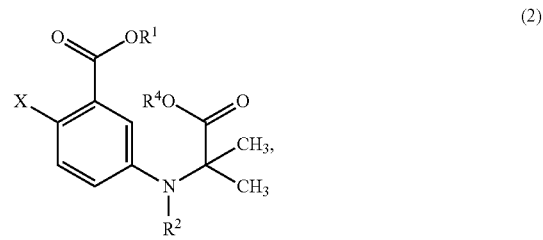

(2)

or a salt thereof,
wherein:
  R$^1$ represents a hydrogen atom, an alkyl group, a cycloalkyl group or an aryl group;
  R$^2$ represents a hydrogen atom, an alkyl group, a hydroxy group or a tert-butoxycarbonyl group;
  R$^4$ represents an alkyl group, a cycloalkyl group or an aryl group; and
  X represents a hydroxy group or a halogen atom;
with a nitrating agent selected from the group consisting of 100% nitric acid, sodium nitrate and potassium nitrate, to obtain a compound represented by formula (3):

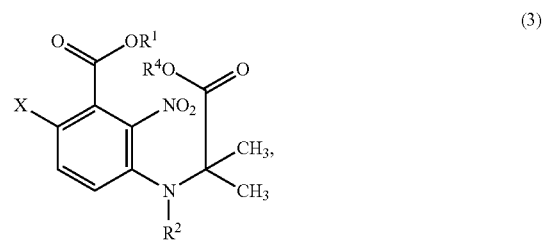

(3)

or a salt thereof, wherein:
R¹ represents a hydrogen atom, an alkyl group, a cycloalkyl group or an aryl group;
R² represents a hydrogen atom, an alkyl group, a hydroxy group or a tert-butoxycarbonyl group;
R⁴ represents an alkyl group, a cycloalkyl group or an aryl group; and
X represents a hydroxy group or a halogen atom; and
(ii) reducing the compound represented by formula (3) above, or a salt thereof, to obtain the compound represented by formula (1), or a salt thereof.

2. The method according to claim 1, further comprising the step of:
reacting a compound represented by formula (6):

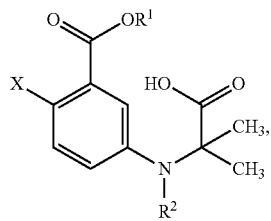  (6)

or a salt thereof,
wherein:
R¹ represents a hydrogen atom, an alkyl group, a cycloalkyl group or an aryl group;
R² represents a hydrogen atom, an alkyl group, a hydroxy group or a tert-butoxycarbonyl group; and
X represents a hydroxy group or a halogen atom;
with a compound represented by formula (7):

R⁴—OH   (7), wherein:
R⁴ represents an alkyl group, a cycloalkyl group or an aryl group;
in the presence of an acid, to obtain the compound represented by formula (2), or a salt thereof.

3. The method according to claim 2,
wherein:
R¹ represents a hydrogen atom.

4. The method according to claim 2, further comprising the step of:
reacting a compound represented by formula (4):

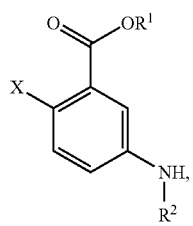  (4)

or a salt thereof,
wherein:
R¹ represents a hydrogen atom, an alkyl group, a cycloalkyl group or an aryl group;
R² represents a hydrogen atom, an alkyl group, a hydroxy group or a tert-butoxycarbonyl group; and
X represents a hydroxy group or a halogen atom;
with a compound represented by formula (5):

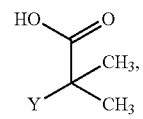  (5)

or a salt thereof,
wherein:
Y represents a hydroxy group or a halogen atom;
to obtain the compound represented by formula (6), or a salt thereof.

5. The method according to claim 1, further comprising the step of:
reacting a compound represented by formula (4):

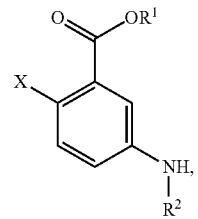  (4)

or a salt thereof,
wherein:
R¹ represents a hydrogen atom, an alkyl group, a cycloalkyl group or an aryl group;
R² represents a hydrogen atom, an alkyl group, a hydroxy group or a tert-butoxycarbonyl group; and
X represents a hydroxy group or a halogen atom;
with a compound represented by formula (5'):

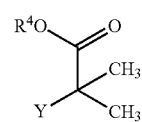  (5')

or a salt thereof,
wherein:
R⁴ represents an alkyl group, a cycloalkyl group or an aryl group; and
Y represents a hydroxy group or a halogen atom;
to obtain the compound represented by formula (2), or a salt thereof.

6. A method for producing a compound represented by formula (1):

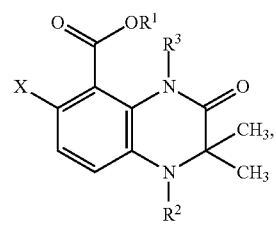  (1)

or a salt thereof, wherein:
R¹ represents a hydrogen atom, an alkyl group, a cycloalkyl group or an aryl group;
R² represents a hydrogen atom, an alkyl group, a hydroxy group or a tert-butoxycarbonyl group;
R³ represents a hydrogen atom, an alkyl group, a hydroxy group or a tert-butoxycarbonyl group; and
X represents a halogen atom;
the method comprising the step of:
reacting a compound represented by formula (8):

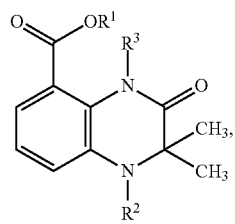

(8)

or a salt thereof,
wherein:
R¹ represents a hydrogen atom, an alkyl group, a cycloalkyl group or an aryl group;
R² represents a hydrogen atom, an alkyl group, a hydroxy group or a tert-butoxycarbonyl group; and
R³ represents a hydrogen atom, an alkyl group, a hydroxy group or a tert-butoxycarbonyl group;
with a halogenating agent selected from the group consisting of chlorine, bromine, 1,3-dibromo-5,5-dimethylhydantoin, N-chlorosuccinimide, N-bromosuccinimide, tetrabutylammonium tribromide, dimethylaminopyridine tribromide and 2,4,4,6-tetrabromo-2,5-cyclohexadienone;
to obtain the compound represented by formula (1), or a salt thereof.

7. The method according to claim 6, further comprising the step of:
reacting a compound represented by formula (9):

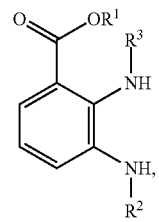

(9)

or a salt thereof,
wherein:
R¹ represents a hydrogen atom, an alkyl group, a cycloalkyl group or an aryl group;
R² represents a hydrogen atom, an alkyl group, a hydroxy group or a tert-butoxycarbonyl group; and
R³ represents a hydrogen atom, an alkyl group, a hydroxy group or a tert-butoxycarbonyl group;
with a compound represented by formula (5″):

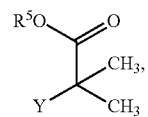

(5″)

or a salt thereof,
wherein:
R⁵ represents a hydrogen atom, an alkyl group, a cycloalkyl group or an aryl group; and
Y represents a hydroxy group or a halogen atom;
to obtain the compound represented by formula (8), or a salt thereof.

* * * * *